(12) United States Patent
Albertella et al.

(10) Patent No.: US 10,960,017 B2
(45) Date of Patent: *Mar. 30, 2021

(54) SORAFENIB OR REGORAFENIB TROXACITABINE PHOSPHORAMIDATE PRODRUG COMBINATION THERAPY FOR LIVER CANCER

(71) Applicant: Medivir Aktiebolag, Huddinge (SE)

(72) Inventors: Mark Albertella, Huddinge (SE); Anders Eneroth, Huddinge (SE); Björn Klasson, Huddinge (SE); Fredrik Öberg, Huddinge (SE); John Öhd, Huddinge (SE)

(73) Assignee: Medivir Aktiebolag, Huddinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/557,511

(22) Filed: Aug. 30, 2019

(65) Prior Publication Data

US 2020/0009166 A1 Jan. 9, 2020

Related U.S. Application Data

(63) Continuation of application No. 16/081,383, filed as application No. PCT/SE2017/050186 on Feb. 28, 2017, now Pat. No. 10,456,413.

(30) Foreign Application Priority Data

Mar. 2, 2016 (SE) .................. 1650274-2
Sep. 8, 2016 (SE) .................. 1651204-8

(51) Int. Cl.
  *A61K 31/675* (2006.01)
  *A61K 31/685* (2006.01)
  *A61K 31/513* (2006.01)
  *A61K 31/44* (2006.01)
  *A61K 9/00* (2006.01)
  *A61P 35/00* (2006.01)

(52) U.S. Cl.
  CPC .......... *A61K 31/685* (2013.01); *A61K 9/0053* (2013.01); *A61K 31/44* (2013.01); *A61K 31/513* (2013.01); *A61K 31/675* (2013.01); *A61P 35/00* (2018.01)

(58) Field of Classification Search
  CPC .. A61K 31/675; A61K 31/685; A61K 31/513; A61K 31/44; A61K 9/00; A61P 35/00
  See application file for complete search history.

(56) References Cited

U.S. PATENT DOCUMENTS 10,030,044 B2 * 7/2018 Dousson ............... C07H 19/207
10,144,750 B2 12/2018 Bethell et al.
10,456,413 B2 * 10/2019 Albertella ............ A61K 9/0053

FOREIGN PATENT DOCUMENTS

| WO | 2002/30922 A2 | 4/2002 |
| WO | WO-2005/009961 A2 | 2/2005 |
| WO | WO-2013/155464 A1 | 10/2013 |
| WO | WO-2014/022116 A2 | 2/2014 |
| WO | 2015/081133 A2 | 6/2015 |
| WO | 2015/081297 A1 | 6/2015 |
| WO | WO-2016/030335 A1 | 3/2016 |
| WO | 2017/151044 A1 | 9/2017 |

OTHER PUBLICATIONS

Bethell et al. "Selective targeting of the liver with nucleotide prodrugs for the treatment of liver cancers", 1 page, retrieved Nov. 26, 2019 from <https://www.medivir.com/media/1198/nucleotide-prodrugs-for-the-treatment-of-liver-cancers.pdf>.
Carlson (2016). "Regorafenib Improves Survival for Unresectable Liver Cancer," Oncology Times, vol. 38, No. 16, p. 27.
Llovet et al. (2008). "Sorafenib in advanced hepatocellular carcinoma", The New England Journal of Medicine (NEJM), Massachusetts Medical Society, US, vol. 359, No. 4, Jul. 24, 2008, pp. 378-390.
Supplementary European Search Report received for EP Application No. 17760400.6, dated Oct. 15, 2019, 12 pages.
International Search Report and Written Opinion received for PCT Patent Application No. PCT/SE2017/050186, dated Jun. 20, 2017, 12 pages.
Mehellou et al., "Aryloxy Phosphoramidate Triesters: A Technology for Delivering Monophosphorylated Nucleosides and Sugars into Cells", ChemMedChem, vol. 4, 2009, pp. 1779-1791.
Notice of Allowance received for U.S. Appl. No. 16/081,383, dated Jun. 17, 2019, 9 pages.
International Preliminary Report on Patentability received for PCT Patent Application No. PCT/SE2017/050186, dated Sep. 13, 2018, 8 pages.

* cited by examiner

*Primary Examiner* — Sun Jae Yoo
(74) *Attorney, Agent, or Firm* — Morrison & Foerster LLP

(57) ABSTRACT

Combination therapy with sorafenib or regorafenib and a phosphoramidate prodrug of troxacitabine with the formula:

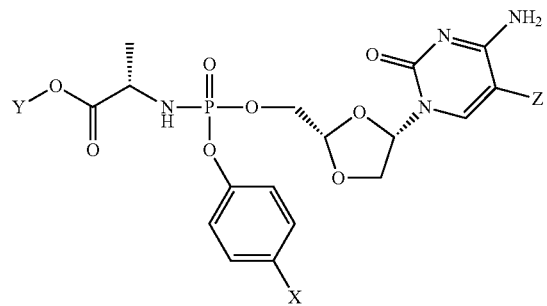

where Y is $C_1$-$C_8$ straight or branched chain alkyl, X is H, halo, $C_3$-$C_4$cycloalkyl or $C_1$-$C_4$alkyl and Z is H or fluoro, or a pharmaceutically acceptable salt thereof, shows surprising utility in the treatment of liver cancer or liver metastasis.

15 Claims, 10 Drawing Sheets

Single P-stereoisomer (10 μM to 0.0015 μM)

Sorafenib (20 μM to 0.31 μM)

Sorafenib (40 μM to 0.62 μM)

Single P-stereoisomer (5 µM to 0.00076 µM)

Sorafenib (20 µM to 0.31 µM)

Single P-stereoisomer (5 µM to 0.00076 µM)

Sorafenib (20 µM to 0.31 µM)

SORAFENIB OR REGORAFENIB TROXACITABINE PHOSPHORAMIDATE PRODRUG COMBINATION THERAPY FOR LIVER CANCER

CROSS REFERENCE TO RELATED APPLICATIONS

This application is a Continuation Application of U.S. patent application Ser. No. 16/081,383, filed Aug. 30, 2018; which is a U.S. National Phase patent application under 35 U.S.C. § 371 of PCT/SE2017/050186, filed Feb. 28, 2017, which claims priority to Sweden Patent Application No. SE 1650274-2, filed Mar. 2, 2016, and Sweden Patent Application No. SE 1651204-8, filed Sep. 8, 2016, the disclosures of each of which are incorporated herein by reference in their entirety.

FIELD OF THE INVENTION

The invention relates to combination therapy for cancer, and more specifically, to sorafenib-troxacitabine phosphoramidate prodrug combination therapy and regorafenib-troxacitabine phosphoramidate prodrug combination therapy for liver cancer and liver metastases.

BACKGROUND OF THE INVENTION

Liver cancer (or hepatic cancer) is a cancer that originates in the liver. Primary liver cancer is the fifth most frequently diagnosed cancer globally and the second leading cause of cancer death. Liver cancers are malignant tumours that grow on the surface or inside the liver. They are formed from either the liver itself or from structures within the liver, including blood vessels or the bile duct.

The leading cause of liver cancer is viral infection with hepatitis B virus or hepatitis C virus. The cancer usually forms secondary to cirrhosis caused by these viruses. For this reason, the highest rates of liver cancer occur where these viruses are endemic, including East-Asia and sub-Saharan Africa. Liver cancers should not be confused with liver metastases, also known as secondary liver cancer, which is a cancer that originate from organs elsewhere in the body and migrate to the liver.

The most frequent liver cancer, accounting for approximately 75% of all primary liver cancers, is hepatocellular carcinoma (HCC). HCC is a cancer formed by liver cells, known as hepatocytes that become malignant. Another type of cancer formed by liver cells is hepatoblastoma, which is specifically formed by immature liver cells. It is a rare malignant tumour that primarily develops in children, and accounts for approximately 1% of all cancers in children and 79% of all primary liver cancers under the age of 15.

Liver cancer can also form from other structures within the liver such as the bile duct, blood vessels and immune cells. Cancer of the bile duct (cholangiocarcinoma and cholangiocellular cystadenocarcinoma) accounts for approximately 6% of primary liver cancers. There is also a variant type of HCC that consists of both HCC and cholangiocarcinoma. Tumours of the liver blood vessels include angiosarcoma and hemangioendothelioma. Embryonal sarcoma and fibrosarcoma are produced from a type of connective tissue known as mesenchyme. Cancers produced from muscle in the liver are leiomyosarcoma and rhabdomyosarcoma. Other less common liver cancers include carcinosarcomas, teratomas, yolk sac tumours, carcinoid tumours and lymphomas. Lymphomas usually have diffuse infiltration to liver, but it may also form a liver mass in rare occasions.

Surgical resection is often the treatment of choice for non-cirrhotic livers. Increased risk of complications such as liver failure can occur with resection of cirrhotic livers. 5-year survival rates after resection has massively improved over the last few decades and can now exceed 50%. Recurrence rates after resection due to the spread of the initial tumour or formation of new tumours exceeds 70%. Liver transplantation can also be used in cases of HCC where this form of treatment can be tolerated and the tumour fits specific criteria (e.g., the Milan criteria). Less than 30-40% of individuals with HCC are eligible for surgery and transplant because the cancer is often detected late stage. Also, HCC can progress during the waiting time for liver transplants, which can ultimately prevent a transplant.

Percutaneous ablation is the only non-surgical treatment that can offer cure. There are many forms of percutaneous ablation, which consist of either injecting chemicals into the liver (ethanol or acetic acid) or producing extremes of temperature using radio frequency ablation, microwaves, lasers or cryotherapy. Of these, radio frequency ablation has one of the best reputations in HCC, but the limitations include inability to treat tumours close to other organs and blood vessels due to heat generation and the heat sync effect, respectively.

Systemic chemotherapeutics are not routinely used in HCC, although local chemotherapy may be used in a procedure known as transarterial chemoembolization (TACE). In this procedure, cytotoxic drugs such as doxorubicin or cisplatin with lipiodol are administered and the arteries supplying the liver are blocked by gelatine sponge or other particles. Because most systemic drugs have no efficacy in the treatment of HCC, research into the molecular pathways involved in the production of liver cancer produced sorafenib, a targeted therapy drug that prevents cell proliferation and blood cell growth in some circumstances. In further research, the fluoro analogue of sorafenib, regorafenib was produced. Regorafenib is a targeted therapy drug that is an oral receptor tyrosine kinase inhibitor which blocks an important pathway that promotes cell division.

Radiotherapy is not often used in HCC because the liver is not tolerant to radiation. Even with modern technology providing well targeted radiation to specific areas of the liver, collateral damage to surrounding liver tissue is a problem, emphasizing the need for better, "liver sparing" regimens. Dual treatments of radiotherapy plus chemoembolization, local chemotherapy, systemic chemotherapy or targeted therapy drugs may show benefit over radiotherapy alone.

Sorafenib (marketed as NEXAVAR®), is an FDA-approved drug for patients with advanced primary liver cancer. It is a small molecule interacting with multiple intracellular and cell surface kinases including the Raf/Mek/Erk pathway. By inhibiting these kinases, genetic transcription involving cell proliferation and angiogenesis is inhibited, with the intriguing observation that hypoxia in solid tumour tissues may be increased due to the treatment reducing blood supply to the tumour. However, even with the development of drugs like sorafenib, the current treatment options for liver cancer are insufficient due to its limited effectiveness and severe toxicity.

Regorafenib (marketed as STIVARGA®), is an FDA-approved drug for metastatic colorectal cancer patients who failed with standard treatments, and for patients with advanced gastrointestinal stromal tumors (GIST) that cannot be surgically removed and no longer respond to other FDA-approved treatments for this disease. Regorafenib has also shown positive results in terms of time to progress (TTP) and overall survival(OS) in a phase II clinical trial as a second-line drug for patients with liver cancer who progress after sorafenib treatment.

Troxacitabine, (beta-L-dioxolane cytidine) is a cytotoxic deoxycytidine analogue with an unnatural L-configuration which has demonstrated broad activity against both solid and hematopoietic malignancies in vitro and in vivo. Particularly, impressive activity has been observed against human cancer cell lines and xenografts of hepatocellular, prostate, and renal origin (Cancer Res., 55, 3008-3011, 1995). Troxacitabine treatment has shown to give rise to a resistance mutation of the kinase deoxycytidine kinase (dCK) which is normally responsible for the first phosphorylation step of the nucleoside, leading to no or very low levels of troxacitabine monophosphate.

Troxacitabine entered phase III clinical trials in 2008 in the acute myelogenous leukemia indication, but did not proceed to registration. Discontinued phase II trials with troxacitabine include breast cancer, colorectal cancer, pancreatic cancer, melanoma, NSCLC, renal, prostate and ovarian tumours. Troxacitabine was generally administered as an intravenous infusion, thereby exposing many tissues to the drug, irrespective of the site of the cancer. It is believed that the clinical development of troxacitabine has been abandoned.

SUMMARY OF THE INVENTION

The invention is based, at least in part, on the discovery that certain combinations of sorafenib and specific phosphoramidate prodrugs of troxacitabine are particularly effective at inhibiting, and preventing the proliferation of, liver cancer cells. This discovery can be described as a synergy, or greater than additive effect, that is specific to sorafenib and these phosphoramidate prodrugs of troxacitabine, within the area of liver cancer (e.g., HCC). We hypothesise that this beneficial interaction may even extend to the treatment of liver metastases.

Without wishing to be bound by theory, we further hypothesise that the unexpectedly profound anti-oncogenic activity of the combination of sorafenib and the specified phosphoramidate prodrugs of troxacitabine, might be further enhanced because the local hypoxia in hepatic tissues generated by sorafenib would enhance the metabolic activation of the troxacitabine prodrug to its cytotoxic triphosphate.

An additional aspect of the invention is based, at least in part, on the discovery that certain combinations of regorafenib and specific phosphoramidate prodrugs of troxacitabine are particularly effective at inhibiting, and preventing the proliferation of, liver cancer cells. This discovery can be described as a synergy, or greater than additive effect, that is specific to regorafenib and these phosphoramidate prodrugs of troxacitabine, within the area of liver cancer (e.g., HCC). We hypothesise that this beneficial interaction may even extend to the treatment of liver metastases.

Without wishing to be bound by theory, we further hypothesise that the unexpectedly profound anti-oncogenic activity of the combination of regorafenib and the specified phosphoramidate prodrugs of troxacitabine, might be further enhanced because the local hypoxia in hepatic tissues generated by regorafenib would enhance the metabolic activation of the troxacitabine prodrug to its cytotoxic triphosphate.

Accordingly, the invention provides methods and compositions for treating liver cancer and liver metastases, whereby sorafenib and a phosphoramidate prodrug of troxacitabine, as defined herein, are administered in combination to human or mammalian individuals.

Additionally, the invention provides methods and compositions for treating liver cancer and liver metastases, whereby regorafenib and a phosphoramidate prodrug of troxacitabine, as defined herein, are administered in combination to human or mammalian individuals.

Sorafenib

The invention, in various aspects and embodiments, includes the use of sorafenib (i.e., sorafenib tosylate as well as other pharmaceutically acceptable forms, salts, and esters of sorafenib). Sorafenib is commercially available as NEXAVAR®, which is the tosylate salt of sorafenib. Sorafenib tosylate has the chemical name 4-(4-{3-[4-Chloro-3(trifluoromethyl)phenyl]ureido}phenoxy) N-methylpyridine-2-carboxamide 4-methylbenzenesulfonate and its structural formula is:

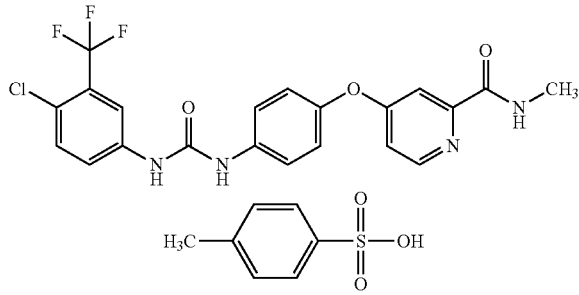

Sorafenib tosylate is a white to yellowish or brownish solid with a molecular formula of $C_{21}H_{16}ClF_3N_4O_3 \times C_7H_8O_3S$ and a molecular weight of 637.0 g/mol. Sorafenib tosylate is practically insoluble in aqueous media, slightly soluble in ethanol and soluble in PEG 400. Sorafenib is also described in U.S. Pat. Nos. 7,235,576, 7,235,576, 7,897,623 and 8,124,630.

Dosage and administration of sorafenib is approved for 400 mg (2 tablets) orally twice daily without food. However, treatment interruption and/or dose reduction may be needed to manage suspected adverse drug reactions. In such cases, dose may be reduced to 400 mg once daily or to 400 mg every other day (see, e.g., the FDA label for NEXAVAR® tablets, oral, Initial U.S. Approval: 2005). A person of ordinary skill will understand that sorafenib dosage and administration can follow medically approved guidelines, as well medically accepted deviations or alterations to such guidelines. Further description and details on sorafenib dosing and administration are provided in the Combination Chemotherapy section below.

The present invention also includes compounds wherein one or more of the atom(s) is/are replaced by an isotope of that/these atom(s), i.e. an atom having the same atomic number but an atomic mass different from the one(s) typically found in nature. Examples of isotopes that may be incorporated into the compounds of the invention, include but are not limited to isotopes of hydrogen, such as $^2H$ and $^3H$ (also denoted D for deuterium and T for tritium, respectively), carbon, such as $^{11}C$, $^{13}C$ and $^{14}C$, nitrogen, such as $^{13}N$ and $^{15}N$, oxygen, such as $^{15}O$, $^{17}O$ and $^{18}O$, phosphorus, such as $^{31}P$ and $^{32}P$, fluorine, such as $^{18}F$, chlorine, such as $^{36}Cl$ and bromine such as $^{75}Br$, $^{76}Br$, $^{77}Br$ and $^{82}Br$. Isotopically labelled compounds include for example those wherein radioactive isotopes, such as $^3$H and $^{14}$C are present, or those wherein non-radioactive isotopes, such as $^2$H and $^{13}$C are present.

The choice of isotope included in an isotope-containing compound will depend on the specific application of that compound. For example, for drug or substrate tissue distribution assays or in metabolic studies compounds wherein a radioactive isotope such as $^3$H or $^{14}$C is incorporated, will generally be most useful. For radio-imaging applications, for example positron emission tomography (PET) a positron emitting isotope such as $^{11}$C, $^{18}$F, $^{13}$N or $^{15}$O will be useful. The incorporation of a heavier isotope, such as deuterium, i.e. $^2$H, may provide certain therapeutic advantages resulting from greater metabolic stability to a compound of the invention, which may result in, for example, an increased in vivo half life of the compound, reduced dosage requirements or an improvement in therapeutic index.

Isotopically-labelled compounds of formula I or any subgroup of formula I can generally be prepared by conventional techniques known to those skilled in the art or by processes analogous to those described in the Schemes and/or Examples herein by using the appropriate isotopically-labelled reagents or starting material instead of the corresponding non-isotopically-labelled reagent or starting material.

In one embodiment, the invention includes deuterated omega diphenylurea or salts thereof, and more particularly to donafenib, 4-(4-(3-(4-chloro-3-(trifluoromethyl)phenyl)ureido)phenoxy)-N-1',1',1'-trideuteromethylpicolinamide or salts thereof, i.e. a compound having the structural formula:

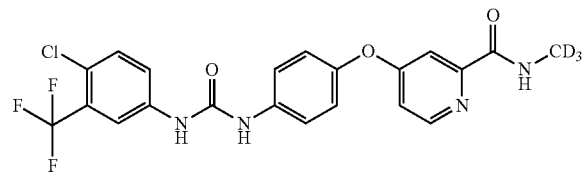 [SMILES: [2H]C([2H])([2H])NC(=O)c1cc(Oc2ccc(NC(=O)Nc3ccc(Cl)c(C(F)(F)F)c3)cc2)ccn1]

Donafenib and the synthesis thereof is extensively disclosed in e.g. WO2011/113367 and WO2014/012480.

Regorafenib

The invention, in various aspects and embodiments, includes the use of regorafenib (i.e., regorafenib monohydrate as well as other pharmaceutically acceptable forms, salts, and esters of regorafenib). Regorafenib is commercially available as STIVARGA®, which is the monohydrate of regorafenib. Regorafenib monohydrate has the chemical name 4-[4-({[4-chloro-3-(trifluoromethyl) phenyl] carbamoyl} amino)-3-fluorophenoxy]-N-methylpyridine-2-carboxamide monohydrate and its structural formula is:

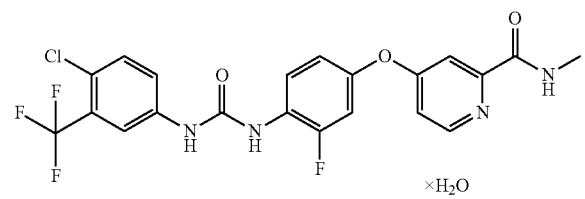 [SMILES: CNC(=O)c1cc(Oc2ccc(NC(=O)Nc3ccc(Cl)c(C(F)(F)F)c3)c(F)c2)ccn1]

Regorafenib monohydrate is a solid with a molecular formula of $C_{21}H_{15}ClF_4N_4O_3 \times H_2O$ and a molecular weight of 500.83 g/mol. Regorafenib monohydrate is practically insoluble in aqueous media, slightly soluble in acetonitrile, methanol, ethanol, and ethyl acetate and sparingly soluble in acetone. Regorafenib is also described in i.a. WO2004/113274, WO2005/000284 and WO2005009961.

Phosphoramidate Prodrugs of Troxacitabine

The phosphoramidate prodrugs of troxacitabine used within the scope of the invention are typically represented by Formula (I):

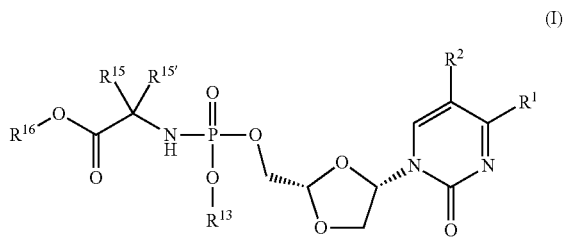

wherein:
$R^1$ is $OR^{11}$, or $NR^5R^{5'}$;
$R^2$ is H or F;
$R^5$ is H, $C_1$-$C_6$alkyl, OH, $C(=O)R^6$, $O(C=O)R^6$ or $O(C=O)OR^6$;
$R^{5'}$ is H or $C_1$-$C_6$alkyl;
$R^6$ is $C_1$-$C_{22}$alkyl or $C_3$-$C_7$cycloalkyl;
$R^{11}$ is H or $C_1$-$C_6$alkyl;
$R^{13}$ is H, phenyl, pyridyl, benzyl, indolyl or naphthyl wherein the phenyl, pyridyl, benzyl, indolyl and naphthyl is optionally substituted with 1, 2 or 3 $R^{22}$;
$R^{15}$ is H, $C_1$-$C_6$alkyl, $C_3$-$C_7$cycloalkyl, $C_3$-$C_7$cycloalkyl$C_1$-$C_3$alkyl, phenyl, benzyl or indolyl;
$R^{15'}$ is H or $C_1$-$C_6$alkyl; or
$R^{15}$ and $R^{15'}$ together with the carbon atom to which they are attached form a $C_3$-$C_7$cycloalkylene group, wherein each $C_1$-$C_6$alkyl is optionally substituted with a group selected from halo, $OR^{18}$ and $SR^{18}$, and each $C_3$-$C_7$cycloalkyl, $C_3$-$C_7$cycloalkylene, phenyl and benzyl is optionally substituted with one or two groups independently selected from $C_1$-$C_3$alkyl, halo and $OR^{18}$;
$R^{16}$ is H, $C_1$-$C_{10}$alkyl, $C_2$-$C_{10}$alkenyl, $C_3$-$C_7$cycloalkyl, $C_3$-$C_7$cycloalkyl$C_1$-$C_3$alkyl, benzyl, or phenyl, any of which is optionally substituted with 1, 2 or 3 groups, each independently selected from halo, $OR^{18}$ and $N(R^{18})_2$;
each $R^{18}$ is independently H, $C_1$-$C_6$alkyl, $C_1$-$C_6$haloalkyl or $C_3$-$C_7$cycloalkyl;
each $R^{22}$ is independently selected from halo, $C_1$-$C_6$alkyl, $C_2$-$C_6$alkenyl, $C_1$-$C_6$haloalkyl, $C_1$-$C_6$alkoxy, $C_1$-$C_6$haloalkoxy, phenyl, hydroxy$C_1$-$C_6$alkyl, $C_3$-$C_6$cycloalkyl, $C_1$-$C_6$alkylcarbonyl, $C_3$-$C_6$cycloalkylcarbonyl, $C_1$-$C_3$alkoxycarbonyl$C_1$-$C_6$alkyl, carboxy$C_1$-$C_6$alkyl, hydroxy, amino CN, and $NO_2$, or any two $R^{22}$ groups attached to adjacent ring carbon atoms can combine to form —O—$(CR^{23}R^{23'})_{1-6}$—O—;
$R^{23}$ and $R^{23'}$ are independently H or $C_1$-$C_3$alkyl;
or a pharmaceutically acceptable salt and/or solvate thereof.

The compounds of Formula (I) may optionally be provided in the form of a pharmaceutically acceptable salt and/or solvate, or as the free form.

In typical embodiments of the invention, $R^1$ is $NR^5R^{5'}$, such as $NH_2$ or $NHC(=O)C_1$-$C_6$alkyl.

$R^2$ is typically H.

In preferred embodiments, $R^1$ is $NH_2$ and $R^2$ is H.

In alternative embodiments, $R^1$ is $NH_2$ and $R^2$ is F.

Typically in compounds of formula (I), the moiety —$NHC(R^{15})(R^{15'})$—$C(=O)OR^{16}$ forms an amino acid ester residue, including natural and non-natural amino acid residues. Of particular interest are amino acid residues wherein $R^{15'}$ is hydrogen and $R^{15}$ is methyl, isopropyl, isobutyl or benzyl. In a typical configuration, $R^{15'}$ is H and $R^{15}$ is $C_1$-$C_3$alkyl, such as methyl, ethyl, propyl, isopropyl.

In compounds wherein $R^{15'}$ is hydrogen and $R^{15}$ is other than hydrogen, the configuration at the asymmetric carbon atom is typically that of an L-amino acid, thus providing compounds having the stereochemistry indicated in formula (Ia):

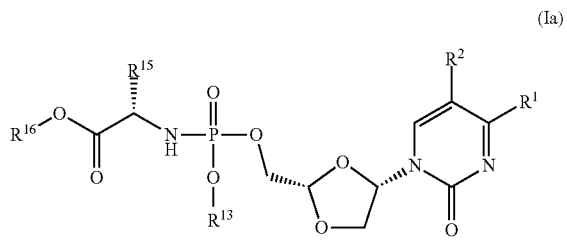

(Ia)

In a preferred configuration of compounds of formula Ia, $R^{15}$ is methyl.

In a further configuration of compounds of formula Ia, $R^{15}$ is benzyl.

In a representative configuration of compounds of formula Ia,
$R^1$ is $NH_2$;
$R^2$ is H;
$R^{13}$ is phenyl naphthyl or indolyl, any of which is optionally substituted with halo e.g. bromo or $C_3$-$C_4$cycloalkyl e.g. cyclopropyl;
$R^{15}$ is $C_1$-$C_3$alkyl
$R^{16}$ is $C_1$-$C_8$alkyl In a further representative configuration of compounds of formula Ia,
$R^1$ is $NH_2$;
$R^2$ is H;
$R^{13}$ is naphthyl;
$R^{15}$ is $C_1$-$C_3$alkyl;
$R^{16}$ is $C_1$-$C_8$alkyl or benzyl;

In a further representative configuration of compounds of formula Ia,
$R^1$ is $NH_2$;
$R^2$ is H;
$R^{13}$ is phenyl which is optionally substituted in the 4-position with halo e.g. bromo or with $C_3$-$C_4$cycloalkyl, e.g. cyclopropyl;
$R^{15}$ is methyl;
$R^{16}$ is $C_3$-$C_8$alkyl.

In a further representative configuration of compounds of formula Ia,
$R^1$ is $NH_2$;
$R^2$ is H;
$R^{13}$ is phenyl;
$R^{15}$ is methyl;
$R^{16}$ is $C_3$-$C_8$alkyl In a further representative configuration of compounds of formula Ia,
$R^1$ is $NH_2$;
$R^2$ is F;
$R^{13}$ is phenyl naphthyl or indolyl, any of which is optionally substituted with halo e.g. bromo or $C_3$-$C_4$cycloalkyl e.g. cyclopropyl;
$R^{15}$ is $C_1$-$C_3$alkyl
$R^{16}$ is $C_1$-$C_8$alkyl In a further representative configuration of compounds of formula Ia,
$R^1$ is $NH_2$;
$R^2$ is F;
$R^{13}$ is naphthyl;
$R^{15}$ is $C_1$-$C_3$alkyl;
$R^{16}$ is $C_1$-$C_8$alkyl or benzyl;

In a further representative configuration of compounds of formula Ia,
$R^1$ is $NH_2$;
$R^2$ is F;
$R^{13}$ is phenyl which is optionally substituted in the 4-position with halo e.g. bromo or with $C_3$-$C_4$cycloalkyl, e.g. cyclopropyl;
$R^{15}$ is methyl;
$R^{16}$ is $C_3$-$C_8$alkyl.

In a further representative configuration of compounds of formula Ia,
$R^1$ is $NH_2$;
$R^2$ is F;
$R^{13}$ is phenyl;
$R^{15}$ is methyl;
$R^{16}$ is $C_3$-$C_8$alkyl In a further configuration, $R^{15}$ and $R^{15'}$ together with the carbon atom to which they are attached form $C_3$-$C_7$cycloalkyl, for example cyclopropyl or cyclobutyl.

$R^{16}$ is typically $C_1$-$C_{10}$alkyl or $C_3$-$C_7$cycloalkyl.

Representative values for $R^{16}$ include $C_1$-$C_3$alkyl, such as methyl, ethyl, propyl, isopropyl. A preferred value for $R^{16}$ is methyl, a further preferred value for $R^{16}$ is isopropyl.

In one embodiment, $R^{16}$ is $C_3$-$C_{10}$alkyl.

Representative values for $R^{16}$ according to this embodiment include branched $C_5$-$C_8$alkyl. In one embodiment, the branching point of $R^{16}$ is at $C_1$. In an alternative embodiment, the branching point of $R^{16}$ is at $C_2$. Typically according to these embodiments, $R^{15'}$ is H, and the stereochemistry at the carbon atom to which $R^{15}$ is attached is that of an L-amino acid, thus providing compounds of the general formulae:

(Ia')

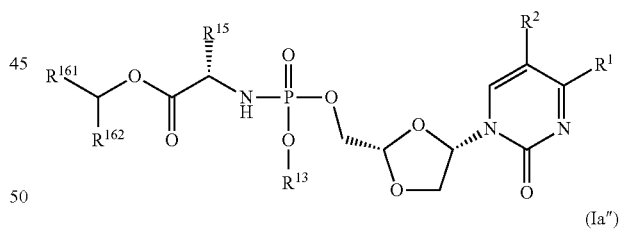

(Ia")

wherein $R^{161}$ and $R^{162}$ are the same or different $C_1$-$C_3$alkyl, and $R^{163}$ and $R^{164}$ are the same or different $C_1$-$C_3$alkyl.

Typically in compounds of formula (Ia'), $R^{16}$ is pentan-2-yl, i.e. $R^{161}$ is propyl and $R^{162}$ is methyl.

In a further typical configuration of compounds of formula (Ia'), $R^{16}$ is butan-2-yl, i.e. $R^{161}$ is ethyl and $R^{162}$ is methyl.

Typically in compounds of formula (Ia″), $R^{16}$ is 2-propylpentyl or 2-ethylbutyl, i.e. $R^{163}$ and $R^{164}$ are both propyl or ethyl respectively.

Further representative values for $R^{16}$ include $C_3$-$C_7$cycloalkyl, such as cyclohexyl.

A further representative value for $R^{16}$ is cyclopentyl.

A further representative value for $R^{16}$ is benzyl.

$R^{13}$ is typically phenyl, naphthyl or indolyl, any of which is optionally substituted with 1 or 2 $R^{22}$.

In one embodiment of the invention, $R^{13}$ is phenyl or naphthyl any of which is optionally substituted.

In one embodiment of the invention, $R^{13}$ is naphthyl.

In a preferred embodiment of the invention, $R^{13}$ is phenyl.

Representative examples of $R^{13}$ include phenyl which is optionally substituted with one, two or three $R^{22}$, thus providing compounds of the formula (II):

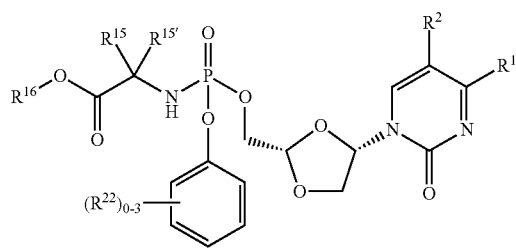

wherein each $R^{22}$, when present, is independently selected from halo, $C_1$-$C_6$alkyl, $C_2$-$C_6$alkenyl and $C_1$-$C_6$alkoxy. Typically, the phenyl ring is unsubstituted or substituted with one $R^{22}$.

In one configuration of compounds of Formula (II), the phenyl ring is unsubstituted.

In a further configuration of compounds of Formula (II), the phenyl ring is substituted with one $R^{22}$. Typically in this configuration, the substituent $R^{22}$ is located to the 4-position of the phenyl ring.

In one embodiment of compounds of the inventions, $R^{13}$ is phenyl which is substituted in the 4-position with halo, e.g. bromo or with $C_3$-$C_4$cycloalkyl, e.g. cyclopropyl.

In one configuration of compounds of Formula (II), the phenyl ring is substituted with $C_1$-$C_3$ alkoycarbonyl$C_1$-$C_3$alkyl. A representative example of this configuration is illustrated in the partial formula:

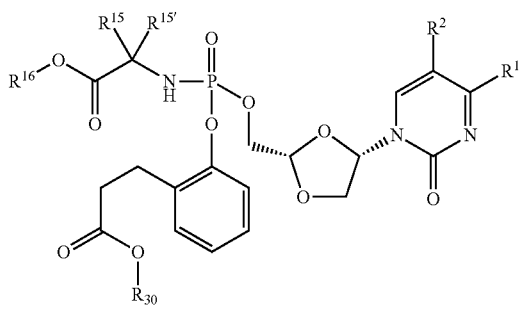

where $R^{30}$ is $C_1$-$C_3$ alkyl, such as methyl or isopropyl.

In a further configuration of compounds of Formula (II), the phenyl ring is substituted with two $R^{22}$ located on adjacent carbon atoms and the two $R^{22}$ combine to form —O—$CH_2$—O—, thus forming the partial structure:

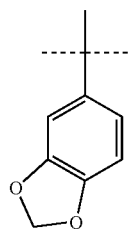

Further representative values for $R^{13}$ include optionally substituted pyridyl. Typically, the pyridyl moiety is unsubstituted or substituted with one or two substituents each independently selected from halo, $C_1$-$C_6$haloalkyl, $C_1$-$C_6$alkyl, $C_2$-$C_6$alkenyl, $C_1$-$C_6$alkoxy, hydroxy, amino.

In a typical embodiment of compounds of formula (I),
$R^1$ is $NH_2$ or NHC(=O)$C_1$-$C_6$alkyl;
$R^{13}$ is phenyl, naphthyl or indolyl, any of which is optionally substituted with halo, $C_1$-$C_3$alkyl, $C_1$-$C_3$alkoxy, $C_3$-$C_6$cycloalkyl or $C_1$-$C_3$haloalkyl;
$R^{15'}$ is H and $R^{15}$ is $C_1$-$C_3$alkyl or benzyl;
$R^{16}$ is $C_1$-$C_{10}$alkyl or $C_3$-$C_7$cycloalkyl.

In a typical embodiment of compounds of formula (I) or (Ia),
$R^1$ is $NH_2$ or NHC(=O)$C_1$-$C_6$alkyl;
$R^{13}$ is phenyl or naphthyl, any of which is optionally substituted with halo, $C_1$-$C_3$alkyl, $C_1$-$C_3$alkoxy, $C_3$-$C_6$cycloalkyl or $C_1$-$C_3$haloalkyl;
$R^{15'}$ is H and $R^{15}$ is $C_1$-$C_3$alkyl or benzyl;
$R^{16}$ is $C_2$-$C_{10}$alkyl or $C_3$-$C_7$cycloalkyl.

In a further typical embodiment of compounds of formula (I),
$R^1$ is $NH_2$;
$R^2$ is H;
$R^{13}$ is phenyl;
$R^{15'}$ is H and $R^{15}$ is $C_1$-$C_3$alkyl;
$R^{16}$ is $C_1$-$C_3$alkyl or cyclohexyl.

In a further typical embodiment of compounds of Formula (I) or (Ia),
$R^1$ is $NH_2$;
$R^2$ is H;
$R^{13}$ is phenyl;
$R^{15'}$ is H and $R^{15}$ is $C_1$-$C_3$alkyl or benzyl;
$R^{16}$ is $C_3$-$C_8$alkyl, cyclopentyl or cyclohexyl.

In a preferred embodiment, the invention provides a method for the treatment of liver cancer or liver metastases in a human or mammal comprising administering in combination (as further defined herein) sorafenib and a phosphoramidate prodrug of troxacitabine with the formula:

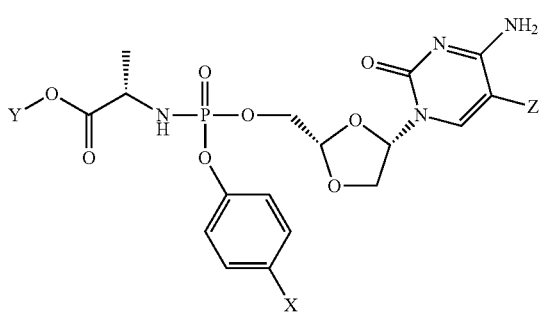

where Y is $C_1$-$C_8$ straight or branched chain alkyl, X is H, halo, $C_3$-$C_4$cycloalkyl or $C_1$-$C_4$alkyl, and Z is H or fluoro, or a pharmaceutically acceptable salt thereof, in the treatment of liver cancer or liver metastases.

In a further embodiment, the invention provides a method for the treatment of liver cancer or liver metastases in a human or mammal comprising administering in combination (as further defined herein) regorafenib and a phosphoramidate prodrug of troxacitabine with the formula:

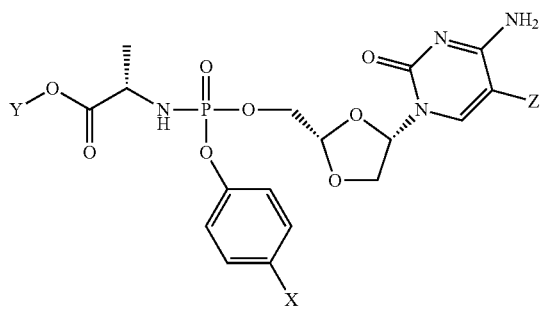

where Y is $C_1$-$C_8$ straight or branched chain alkyl, X is H, halo, $C_3$-$C_4$cycloalkyl or $C_1$-$C_4$alkyl, and Z is H or fluoro, or a pharmaceutically acceptable salt thereof, in the treatment of liver cancer or liver metastases.

In certain embodiments the phosphoramidate prodrug of troxacitabine has the stereochemistry:

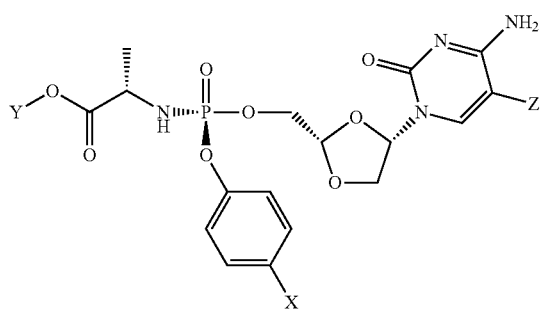

Where X, Y and Z are as defined above.
In preferred embodiments Z is H.
In certain embodiments:
a) X is H and Y is 2-propylpentyl;
b) X is H and Y is (S)-pentan-2-yl;
c) X is Br and Y is (S)-pentan-2-yl;
d) X is H and Y is (R)-sec-butyl;
e) X is H and Y is 2-ethylbutyl;
f) X is cyclopropyl and Y is (S)-pentan-2-yl; or
g) X is t-butyl and Y is (S)-pentan-2-yl,
in each case especially when Z is H.

In alternative embodiments the phosphoramidate prodrug of troxacitabine has the stereochemistry:

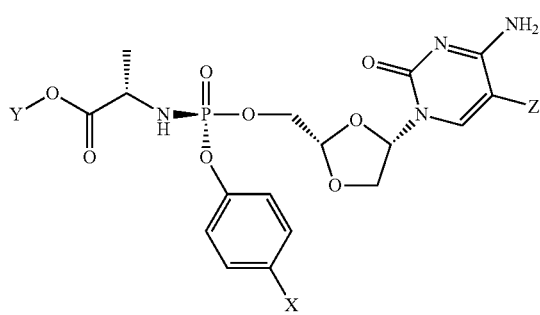

Where X, Y and Z are as defined above.
In preferred embodiments Z is H.
In certain embodiments:
a) X is H and Y is 2-propylpentyl;
b) X is H and Y is (S)-pentan-2-yl;
c) X is Br and Y is (S)-pentan-2-yl;
d) X is H and Y is (R)-sec-butyl;
e) X is H and Y is 2-ethylbutyl;
f) X is cyclopropyl and Y is (S)-pentan-2-yl; or
g) X is t-butyl and Y is (S)-pentan-2-yl,
in each case especially when Z is H.

In certain embodiments the phosphoramidate prodrug of troxacitabine is selected from the compounds depicted below:

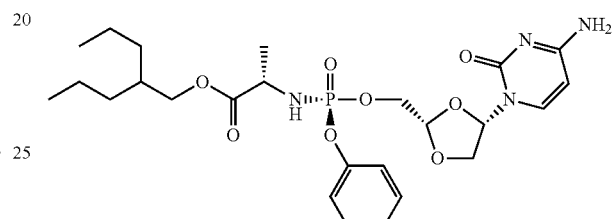

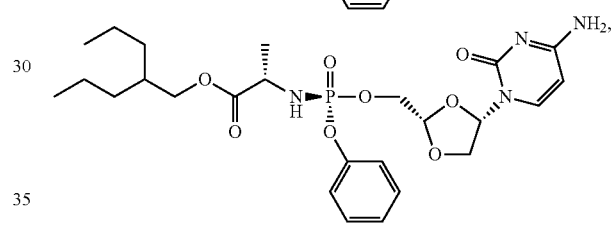

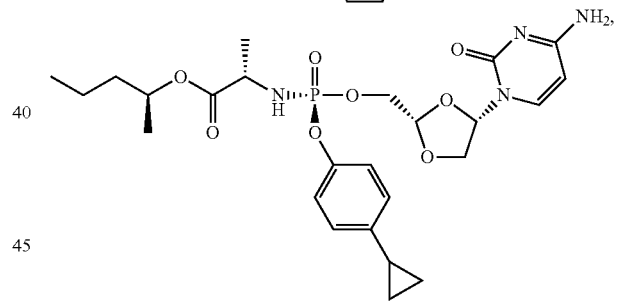

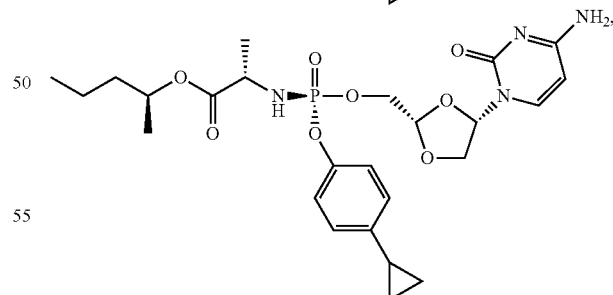

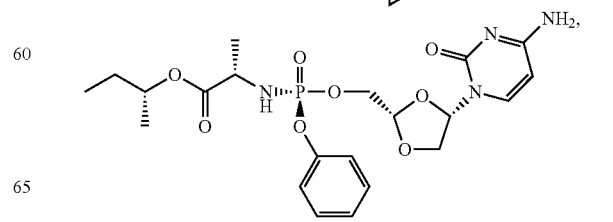

In a typical embodiment the phosphoramidate prodrug of troxacitabine is selected from the compounds depicted below:

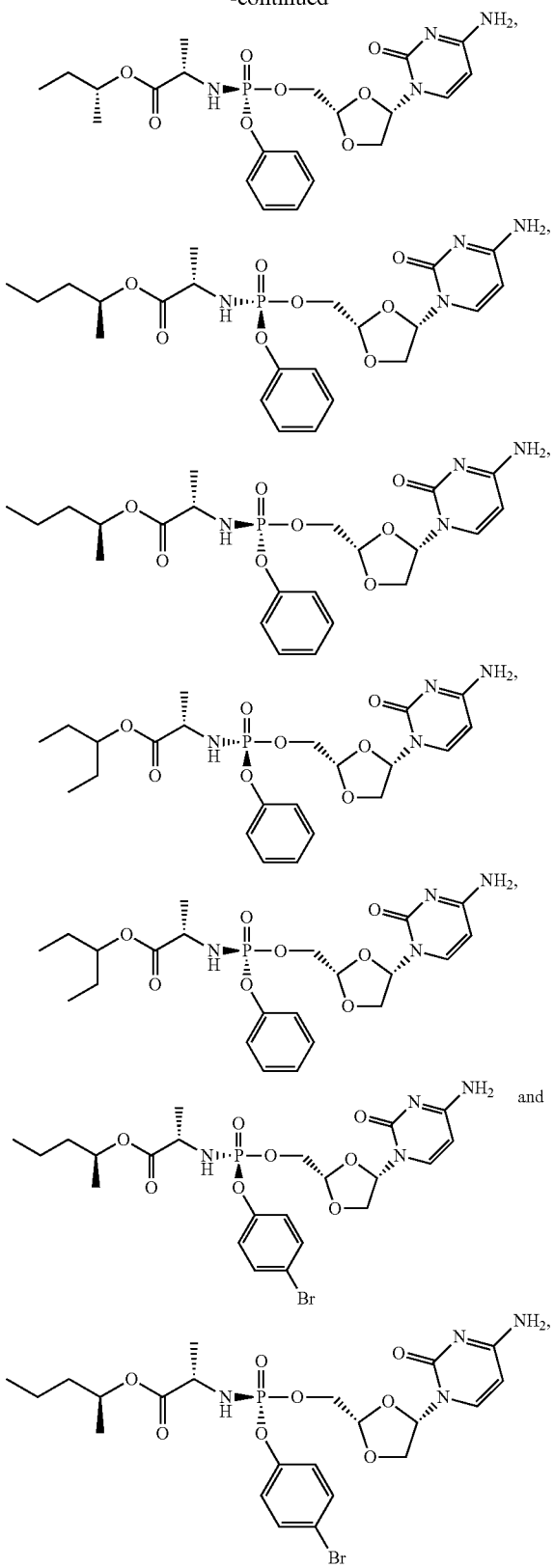

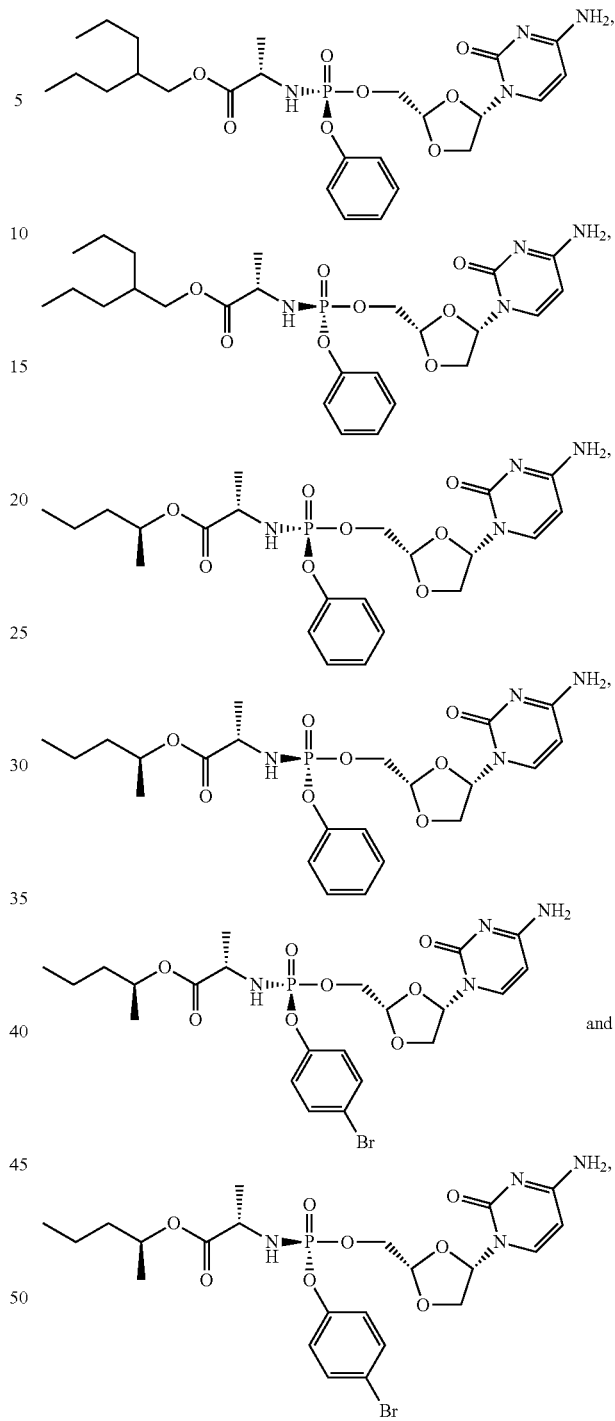

Synthesis methodology for the phosphoramidate prodrug of troxacitabine is extensively described and exemplified in PCT/EP2015/069370 whose contents are incorporated by reference in their entirety Liver Cancer The invention, in various aspects and embodiments, is applicable to the treatment of liver cancer in a subject. which can be a primate, such as a human. The subject can be a mammal, such as mammal other than a mouse. The subject can be an adult human (i.e., 18 years or older), or a juvenile human (i.e., less than 18 years old).

In various embodiments, the liver cancer (e.g., HCC) is not resistant to sorafenib. Alternatively, the liver cancer (e.g., HCC) can have primary or secondary resistance to sorafenib. The subject can be a responder to sorafenib in the absence of the phosphoramidate prodrug of troxacitabine. The subject can be a non-responder to sorafenib in the absence of the phosphoramidate prodrug of troxacitabine. In some embodiments, the subject has undergone a prior treatment with sorafenib lasting at least 2, 4, 6, 8, 10 months or longer. In other embodiments, the subjects are patients who have experienced one or more significant adverse side effect to sorafenib and therefore require a reduction in dose.

In various embodiments, the liver cancer (e.g., HCC) is not resistant to regorafenib. Alternatively, the liver cancer (e.g., HCC) can have primary or secondary resistance to regorafenib. The subject can be a responder to regorafenib in the absence of the phosphoramidate prodrug of troxacitabine. The subject can be a non-responder to regorafenib in the absence of the phosphoramidate prodrug of troxacitabine. In some embodiments, the subject has undergone a prior treatment with regorafenib lasting at least 2, 4, 6, 8, 10 months or longer. In other embodiments, the subjects are patients who have experienced one or more significant adverse side effect to regorafenib and therefore require a reduction in dose.

In various embodiments, the liver cancer (e.g., HCC) is intermediate, advanced, or terminal stage. The liver cancer (e.g., HCC) can be metastatic or non-metastatic. The liver cancer (e.g., HCC) can be resectable or unresectable. The liver cancer (e.g., HCC) can comprise a single tumour, multiple tumours, or a poorly defined tumour with an infiltrative growth pattern (into portal veins or hepatic veins). The liver cancer (e.g., HCC) can comprise a fibrolamellar, pseudoglandular (adenoid), pleomorphic (giant cell), or clear cell pattern. The liver cancer (e.g., HCC) can comprise a well differentiated form, and tumour cells resemble hepatocytes, form trabeculae, cords, and nests, and/or contain bile pigment in cytoplasm. The liver cancer (e.g., HCC) can comprise a poorly differentiated form, and malignant epithelial cells are discohesive, pleomorphic, anaplastic, and/or giant. In some embodiments, the liver cancer (e.g., HCC) is associated with hepatitis B, hepatitis C, cirrhosis, or type 2 diabetes.

In some embodiments, the subject is a human having an Eastern Cooperative Oncology Group (ECOG) performance status <2.

In some embodiments, the subject is a human having acceptable liver function defined as (i) total bilirubin <1.5 times the upper limit of normal (ULN); for patients with hepatocellular carcinoma only, total bilirubin <3 mg/dL (i.e., Child-Pugh Score for bilirubin is no greater than 2); (ii) aspartate aminotransferase (AST), alanine aminotransferase (ALT) and alkaline phosphatase (ALP) <5×ULN; or (iii) acceptable renal function: Serum creatinine <1.5 times the ULN, or calculated creatinine clearance >60 mL/min/1.73 m$^2$ for patients with creatinine levels above 1.5 times the institutional normal.

In some embodiments, the subject is a human having acceptable haematological status defined as (i) absolute Neutrophil Count (ANC) >1500 cells/mm$^3$; (ii) platelet count >100,000 plts/mm$^3$ (without transfusion); >75,000 plts/mm$^3$ for patients with hepatocellular carcinoma only; or (iii) haemoglobin >9 g/dL.

In some embodiments, the subject is a human having a prothrombin time (PT) or International Normalized Ratio (INR) <1.25×ULN; INR <1.7 or prothrombin time (PT) or <4 seconds above ULN (i.e., Child-Pugh Score is no greater than 1 for the coagulation parameter); or serum albumin >2.8 g/dL (i.e., Child-Pugh Score for albumin is no greater than 2).

In some embodiments, the subject is a human having a prothrombin Child-Pugh Class A (score 5-6) disease. Score for hepatic encephalopathy must be 1; the score for ascites must be no greater than 2 and clinically irrelevant; for the determination of the Child-Pugh Class.

In some embodiments, the subject is a human that does not have a New York Heart Association (NYHA) Class III or IV cardiac disease, myocardial infarction within the past 6 months, unstable and/or symptomatic arrhythmia, or evidence of ischemia on ECG.

In some embodiments, the subject does not have an active, uncontrolled bacterial, viral, or fungal infections requiring systemic therapy.

In some embodiments, the subject is a human that is not a pregnant or nursing woman.

In some embodiments, the subject is a human that does not have a known infection with human immunodeficiency virus (HIV).

In some embodiments, the subject is a human that does not have a serious non-malignant disease (e.g., hydronephrosis, liver failure, or other conditions) that could compromise the therapy.

In some embodiments, the subject is a human that does not have a recent history of haemorrhage and patients predisposed to haemorrhage due to coagulopathies or structural anomalies.

In some embodiments, the subject is a human that does not require treatment with therapeutic doses of coumarin-type anticoagulants.

In some embodiments, the subject is a human that does not have a cirrhosis classed as Child-Pugh B or C.

In some embodiments, the subject is a human that wherein the subject has an alpha-fetoprotein (AFP) >10, 50, 100, 200, 300, 400, or 500 ng/mL.

In some embodiments, the subject is a human that wherein the subject has an elevates (>10%) AFP-L3 level.

In some embodiments, the subject is a human that has a Des-Gamma-Carboxy (Abnormal) Prothrombin (DCP) >5, 7.5, 10, 25, 50, 75, or 100 ng/mL.

In some embodiments, the subject is a human that has an abnormal level of an epidermal growth factor receptor (EGFR) (erbB-1), c-erb-2 (Her-2/neu), c-erb-3 (HER-3), c-erb-4 (HER-4), or a combination thereof. [00100] In some embodiments, the subject is a human that has an abnormal level of Alpha-Fetoprotein (AFP); Glypican-3 (GPC3); Des-Gamma-Carboxy (Abnormal) Prothrombin (DCP); Serum gamma-glutamyl transferase (GGT); Alpha-1-fucosidase (AFU); Human Carbonyl Reductase 2; Golgi phosphoprotein 2 (GOLPH2); Transforming Growth Factor-Beta (TGF-Beta); Tumor-Specific Growth Factor (TSGF); Hepatocyte growth factor/scatter factor (HGF/SF); Basic Fibroblast Growth Factor; Alpha-Fetoprotein mRNA (AFP mRNA); Gamma-Glutamyl Transferase mRNA (GGT mRNA); Insulin-Like Growth Factor II (IGF-II) mRNA; Albumin mRNA; DK 1; Golgi protein 73 (GP73); Protein induced by vitamin K absence or antagonist II (PIVKA-II); miR-122, miR-192, miR-21, miR-223, miR-26a, miR-27a, and miR-801, or a combination thereof.

In various embodiments, any of the aspects and embodiments can be combined with any one or more of the features below. For example:

In some embodiments, the liver cancer is primary liver cancer.

In some embodiments, the liver cancer is hepatocellular carcinoma (HCC).

In some embodiments, the liver cancer is intra-hepatic cholangiocarcinoma.

In some embodiments the liver metastasis is derived from colorectal cancer, but also breast cancer, esophageal cancer, lung cancer, melanoma, pancreatic cancer, and stomach cancer.

Combination Chemotherapy

As used herein, the term "administration in combination" is not limited to the situation where both the sorafenib and phosphoramidate prodrug of troxacitabine or the regorafenib and phosphoramidate prodrug of troxacitabine are co-administered to the human or mammal in a common dosage unit such as a tablet or oral suspension, although such common dosage units can have advantages in terms of dosing convenience, patient compliance and accuracy of dose.

More typically the sorafenib and the phosphoramidate prodrug of troxacitabine or the regorafenib and phosphoramidate prodrug of troxacitabine in respective dosage units, allowing the prescribing physician greater freedom of calibration of dose. In the case of sorafenib, commercially available products currently include Nexavar® film coated tablets 200 mg. In the case of regorafenib, commercially available products currently include Stivarga® film coated tablets 40 mg.

The sorafenib dosing amount and/or schedule can follow clinically approved, or experimental, guidelines. In various embodiments, the dose of sorafenib is about 800, 600, 400, or 200 mg/day. A 200 mg/day dose can be administered as a 400 mg dose every other day. Individuals with low body weights such as juveniles and geriatrics will generally be dosed with partial tablets.

The regorafenib dosing amount and/or schedule can follow clinically approved, or experimental, guidelines. In various embodiments, the dose of regorafenib is about 640, 480, 320, or 160 mg/day. A 160 mg/day dose can be administered as a 320 mg dose every other day. Individuals with low body weights such as juveniles and geriatrics will generally be dosed with partial tablets.

The phosphoramidate prodrug of troxacitabine will generally be administered orally, most typically as one or several tablets or capsules, each containing between 10 mg to 600 mg of the active pharmaceutical ingredient. Representative tablets or capsules may contain between 25 mg and 500 mg, or between 50 mg and 450 mg, or between 100 mg and 400 mg, such as between 150 mg and 400 mg, between 200 mg and 500 mg or between 250 mg and 500 mg.

In various embodiments the phosphoramidate prodrug of troxacitabine is administered to the subject in 1, 2, 3, 4, 5, 6, or 7 daily doses over a single week (7 days). The phosphoramidate prodrug of troxacitabine can be administered to the subject in 1, 2, 3, 4, 5, 6, 7, 8, 9, 10, 11, 12, 13, or 14 daily doses over 14 days. The phosphoramidate prodrug of troxacitabine can be administered to the subject in 1, 2, 3, 4, 5, 6, 7, 8, 9, 10, 11, 12, 13, 14, 15, 16, 17, 18, 19, 20, or 21 daily doses over 21 days. The phosphoramidate prodrug of troxacitabine can be administered to the subject in 1, 2, 3, 4, 5, 6, 7, 8, 9, 10, 11, 12, 13, 14, 15, 16, 17, 18, 19, 20, 21, 22, 23, 24, 25, 26, 27, or 28 daily doses over 28 days.

In various embodiments the phosphoramidate prodrug of troxacitabine is administered for: 2 weeks (total 14 days); 1 week with 1 week off (total 14 days); 3 consecutive weeks (total 21 days); 2 weeks with 1 week off (total 21 days); 1 week with 2 weeks off (total 21 days); 4 consecutive weeks (total 28 days); 3 consecutive weeks with 1 week off (total 28 days); 2 weeks with 2 weeks off (total 28 days); 1 week with 3 consecutive weeks off (total 28 days).

In various embodiments the phosphoramidate prodrug of troxacitabine is administered on day 1 of a 7, 14, 21 or 28 day cycle; administered on days 1 and 15 of a 21 or 28 day cycle; administered on days 1, 8, and 15 of a 21 or 28 day cycle; or administered on days 1, 2, 8, and 15 of a 21 or 28 day cycle. The phosphoramidate prodrug of troxacitabine can be administered once every 1, 2, 3, 4, 5, 6, 7, or 8 weeks.

The sorafenib and phosphoramidate prodrug of troxacitabine may be administered substantially simultaneously, as a common dosage unit or respective dosage unit, or the administration in combination may be staggered or alternating, that is with separate cycles of sorafenib and the phosphoramidate prodrug of troxacitabine. For example serial week long cycles of daily sorafenib, may be interspersed with one, two, three, five or seven day cycles of daily phosphoramidate prodrug of troxacitabine.

Alternatively, a loading dose of one agent, for example the sorafenib component, may be commenced, for example to build up local hypoxia in the liver, followed by commencement of co-dosing with the phosphoramidate prodrug of troxacitabine.

It may be convenient to monitor staggered combination administration by reference to a target molar or mg ratio between sorafenib and the phosphoramidate prodrug of troxacitabine. In various embodiments, the ratio (e.g., molar ratio of sorafenib:phosphoramidate prodrug of troxacitabine) is between about 20:1 to 1:20, such as 5:1, 2:1, 1:1, 1:2, 1:5 or 1:10.

The molar ratio of sorafenib:phosphoramidate prodrug of troxacitabine can be measured over different periods of time. For example, the molar ratio can be the amount of sorafenib: phosphoramidate prodrug of troxacitabine administered to the subject in a single day, a single week, 14 days, 21 days, or 28 days.

According to certain embodiments the method of the invention envisages that the sorafenib and the phosphoramidate prodrug of troxacitabine are each administered daily (as QD, BID or TID) on the same day.

In such an embodiment the sorafenib and the phosphoramidate prodrug of troxacitabine may be co-delivered in a common, orally administered dosage unit, such as a capsule, softgel capsule or tablet In other embodiments the method of the invention envisages that the sorafenib and the phosphoramidate prodrug of troxacitabine are administered as separate, orally administered dosage units.

In a representative embodiment of the paragraph immediately above, the dosage unit(s) of sorafenib and the dosage unit(s) of the phosphoramidate prodrug of troxacitabine are administered at least 6 hours apart on any given day, preferably at least 8 hours and typically around 12 hours apart, for patient comfort.

Certain embodiments of the method of the invention envisage that the sorafenib and the phosphoramidate prodrug of troxacitabine are alternately administered in monotherapy treatment cycles of 1-28 days, optionally interspersed with treatment-free periods of 1-28 days.

As used herein "monotherapy" of the sorafenib or the phosphoramidate prodrug of troxacitabine means that sorafenib is not administered during a cycle of the phosphoramidate prodrug of troxacitabine and vice versa. Monotherapy does not preclude the co-administration of other therapeutics (including other anticancer agents or palliatives, all as ordained by the responsible physician.

The regorafenib and phosphoramidate prodrug of troxacitabine may be administered substantially simultaneously, as a common dosage unit or respective dosage unit, or the administration in combination may be staggered or alternating, that is with separate cycles of sorafenib and the phosphoramidate prodrug of troxacitabine. For example serial week long cycles of daily regorafenib, may be interspersed with one, two, three, five or seven day cycles of daily phosphoramidate prodrug of troxacitabine.

Alternatively, a loading dose of one agent, for example the regorafenib component, may be commenced, for example to build up local hypoxia in the liver, followed by commencement of co-dosing with the phosphoramidate prodrug of troxacitabine.

It may be convenient to monitor staggered combination administration by reference to a target molar or mg ratio between regorafenib and the phosphoramidate prodrug of troxacitabine. In various embodiments, the ratio (e.g., molar ratio of regorafenib:phosphoramidate prodrug of troxacitabine) is between about 20:1 to 1:20, such as 5:1, 2:1, 1:1, 1:2, 1:5 or 1:10.

The molar ratio of regorafenib:phosphoramidate prodrug of troxacitabine can be measured over different periods of time. For example, the molar ratio can be the amount of regorafenib:phosphoramidate prodrug of troxacitabine administered to the subject in a single day, a single week, 14 days, 21 days, or 28 days.

According to certain embodiments the method of the invention envisages that the regorafenib and the phosphoramidate prodrug of troxacitabine are each administered daily (as QD, BID or TID) on the same day.

In such an embodiment the regorafenib and the phosphoramidate prodrug of troxacitabine may be co-delivered in a common, orally administered dosage unit, such as a capsule, softgel capsule or tablet In other embodiments the method of the invention envisages that the regorafenib and the phosphoramidate prodrug of troxacitabine are administered as separate, orally administered dosage units.

In a representative embodiment of the paragraph immediately above, the dosage unit(s) of regorafenib and the dosage unit(s) of the phosphoramidate prodrug of troxacitabine are administered at least 6 hours apart on any given day, preferably at least 8 hours and typically around 12 hours apart, for patient comfort.

Certain embodiments of the method of the invention envisage that the regorafenib and the phosphoramidate prodrug of troxacitabine are alternately administered in monotherapy treatment cycles of 1-28 days, optionally interspersed with treatment-free periods of 1-28 days.

As used herein "monotherapy" of the regorafenib or the phosphoramidate prodrug of troxacitabine means that regorafenib is not administered during a cycle of the phosphoramidate prodrug of troxacitabine and vice versa. Monotherapy does not preclude the co-administration of other therapeutics (including other anticancer agents or palliatives, all as ordained by the responsible physician.

As used herein for describing ranges, e.g., of ratios, doses, times, and the like, the terms "about" embraces variations that are within the relevant margin of error, essentially the same (e.g., within an art-accepted confidence interval such as 95% for phenomena that follow a normal or Gaussian distribution), or otherwise does not materially change the effect of the thing being quantified.

A course of sorafenib-phosphoramidate prodrug of troxacitabine therapy or regorafenib-phosphoramidate prodrug of troxacitabine therapy can be prescribed by a clinician.

The phosphoramidate prodrug of troxacitabine (and hence the combination therapy) can be administered for 1, 2, 3, 4, 5, 6, 7, 8, 9, 10, 11, or 12 cycles.

A course of sorafenib-phosphoramidate prodrug of troxacitabine therapy or regorafenib-phosphoramidate prodrug of troxacitabine therapy can be continued until a clinical endpoint is met. In some embodiments, the therapy is continued until disease progression or unacceptable toxicity occurs. In some embodiments, the therapy is continued until achieving a pathological complete response (pCR) rate defined as the absence of liver cancer (e.g., HCC). In some embodiments, the therapy is continued until partial or complete remission of the liver cancer. Administering the phosphoramidate prodrug of troxacitabine and the regorafenib to a plurality of subjects having HCC increases the Overall Survival (OS), the Progression free Survival (PFS), the Disease Free Survival (DFS), the Response Rate (RR), the Quality of Life (QoL), or a combination thereof.

In various embodiments, the treatment reduces the size and/or number of the liver cancer tumour(s). The treatment can prevent the liver cancer tumour(s) from increasing in size and/or number. The treatment can prevent the liver cancer tumour(s) from metastasizing.

In the methods of the invention, administration is not limited to any particular delivery system and may include, without limitation, parenteral (including subcutaneous, intravenous, intramedullary, intraarticular, intramuscular, or intraperitoneal injection), rectal, topical, transdermal, or preferably oral (for example, in capsules, suspensions, or tablets).

Administration to an individual may occur in a single dose or in repeat administrations, and in any of a variety of physiologically acceptable salt forms, and/or with an acceptable pharmaceutical carrier and/or additive as part of a pharmaceutical composition.

Physiologically acceptable salt forms and standard pharmaceutical formulation techniques, dosages, and excipients are well known to persons skilled in the art (see, e.g., Physicians' Desk Reference (PDR®) 2005, 59th ed., Medical Economics Company, 2004; and Remington: The Science and Practice of Pharmacy, eds. Gennado et al. 21th ed., Lippincott, Williams & Wilkins, 2005).

Additionally, effective dosages achieved in one animal may be extrapolated for use in another animal, including humans, using conversion factors known in the art. See, e.g., Freireich et al., Cancer Chemother Reports 50(4):219-244 (1966) and the table below for equivalent surface area dosage factors).

Equivalent Surface Area Dosage Factors

| | From: | | | | |
| --- | --- | --- | --- | --- | --- |
| To: | Mouse (20 g) | Rat (150 g) | Monkey (3.5 kg) | Dog (8 kg) | Human (60 kg) |
| Mouse | 1 | 0.5 | 0.25 | 0.17 | 0.08 |
| Rat | 2 | 1 | 0.5 | 0.25 | 0.14 |
| Monkey | 4 | 2 | 1 | 0.6 | 0.33 |
| Dog | 6 | 4 | 1.7 | 1 | 0.5 |
| Human | 12 | 7 | 3 | 2 | 1 |

The combination therapies of the invention are not specifically limited to any particular course or regimen and may be employed separately or in conjunction with other therapeutic modalities (e.g. chemotherapy or radiotherapy).

A combination therapy in accordance with the present invention can include additional therapies (e.g. pharmaceutical, radiation, and the like) beyond the sorafenib and phosphoramidate prodrug of troxacitabine or the regorafenib and phosphoramidate prodrug of troxacitabine. Similarly, the present invention can be used as an adjuvant therapy (e.g., when combined with surgery). In various embodiments, the subject is also treated by surgical resection, percutaneous ethanol or acetic acid injection, transarterial chemoembolization, radiofrequency ablation, laser ablation, cryoablation, focused external beam radiation stereotactic radiotherapy, selective internal radiation therapy, intra-arterial iodine-131-lipiodol administration, and/or high intensity focused ultrasound.

The combination of the phosphoramidate prodrug of troxacitabine and sorafenib can be used as an adjuvant, neoadjuvant, concomitant, concurrent, or palliative therapy. The combination of the phosphoramidate prodrug of troxacitabine and sorafenib can be used as a first line therapy, second line therapy, or crossover therapy.

The combination of the phosphoramidate prodrug of troxacitabine and regorafenib can be used as an adjuvant, neoadjuvant, concomitant, concurrent, or palliative therapy. The combination of the phosphoramidate prodrug of troxacitabine and regorafenib can be used as a first line therapy, second line therapy, or crossover therapy.

In some embodiments, the therapeutically effective dose of sorafenib is reduced through combination with the phosphoramidate prodrug of troxacitabine. For example, the weekly or monthly dose of sorafenib can be reduced by at least 10%, 20%, 30%, 40%, 50%, 60%, 70%, 80%, 90% or more relative to the maximum recommended dose or the maximum tolerated dose. In other embodiments, sorafenib is administered at an effective dose that is at least 50%, 60%, 70%, 80%, 90% or more below the dose needed to be effective in the absence of the phosphoramidate prodrug of troxacitabine administration. In some embodiments, the $IC_{50}$ of sorafenib is reduced by at least 4-, 5-, 10-, 20-, 30-, 40-, 50-, or 100-fold relative to the $IC_{50}$ in the absence of the phosphoramidate prodrug of troxacitabine.

In some embodiments, the therapeutically effective dose of regorafenib is reduced through combination with the phosphoramidate prodrug of troxacitabine. For example, the weekly or monthly dose of regorafenib can be reduced by at least 10%, 20%, 30%, 40%, 50%, 60%, 70%, 80%, 90% or more relative to the maximum recommended dose or the maximum tolerated dose. In other embodiments, regorafenib is administered at an effective dose that is at least 50%, 60%, 70%, 80%, 90% or more below the dose needed to be effective in the absence of the phosphoramidate prodrug of troxacitabine administration. In some embodiments, the $IC_{50}$ of regorafenib is reduced by at least 4-, 5-, 10-, 20-, 30-, 40-, 50-, or 100-fold relative to the $IC_{50}$ in the absence of the phosphoramidate prodrug of troxacitabine.

Further description and embodiments of combination therapies are provided in the Examples section below.

DETAILED DESCRIPTION OF REPRESENTATIVE EMBODIMENTS

Illustrative embodiments of the invention are described in the following Examples, with reference to the accompanying drawings in which FIG. 1A represents a drug concentration/activity array of the combination of sorafenib and the single phosphorus stereoisomer of the phosphoramidate prodrug of troxacitabine denoted (2S)-2-propylpentyl 2-(((((2S,4S)-4-(4-amino-2-oxopyrimidin-1(2H)-yl)-1,3-dioxolan-2-yl) methoxy)-(phenoxy)phosphoryhamino)propanoate.

Figure 1A:
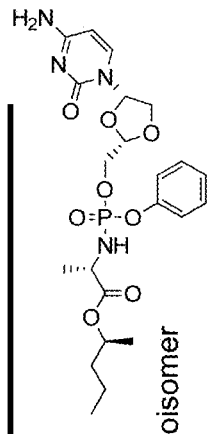
FIG. 1B represents the 3D-synergy plot derived from the data of FIG. 1A.

One of ordinary skill in the art will recognize the numerous modifications and variations that may be performed without altering the spirit or scope of the present invention. Such modifications and variations are encompassed within the scope of the invention. The Examples do not in any way limit the invention.

General Procedure for Combinatorial Evaluation in Cell Culture

Subculture:

For analysis of the human hepatocellular carcinoma cell line Hep3B, from DSMZ (ACC 93), was used. Hep3B cells were cultured as epithelial-like cells in monolayers in 90% MEM (with Earle's salts)+10% h.i. FBS+2 mM L-glutamine+50 u/ml Penicillin/0.05 mg/ml Streptomycin as culture medium. Confluent cultures were split 1:4 to 1:10 every 3-5 days using trypsin/EDTA, and re-seeded at $0.5-1\times10^6$ cells/80 cm$^2$.

Materials:

Complete cell medium without phenol red was used:
DMEM with no phenol red
10% FCS
50 u/ml Penicillin/0.05 mg/ml Streptomycin
Trypsin-EDTA PAA Cat. no. L11-004 from Fisher Scientific
Cell assay plate for adherent cells, 96-well, Cat. no. 128009296 from Fisher Scientific
Sealing Tape, Nunc Cat. no. 732 610 from VWR
Test compounds:
Compounds made up to 10 mM stock solution in DMSO (Carlo Erba Reactifs—SDS, Cat No 03502T16)
Analysis of cell proliferation:
Cell Counting Kit-8 CK04 from Dojindo Instrument:
Echo 550 Acoustic Liquid handler, Labcyte
Tecan sunrise, spectrophotometer
Soft ware (shareware)
MacSynergy II downloaded from https://www.uab.edu/medicine/peds/macsynergy (Prichard, M. N. and C. Shipman, Jr. 1990. (Review) A three-dimensional model to analyze drug-drug interactions. Antiviral Res. 14:181-206.)

Test procedure:
Day 1. Cell seeding:
Cell culture flask is washed 2 times with 5 ml PBS and PBS discarded. Add 1.5 ml of trypsin and put the flask into the incubator for 3-4 minutes. Shake the flask and add 10 ml of DMEM, 10% FCS, 50 µ/ml Penicillin/0.05 mg/ml Streptomycin without phenol red. The cells were counted using the Scepter cell counter, Hep3B cells were diluted to $20 \times 10^3$ cells/ml in complete cell medium without phenol red. 100 µl cell suspension/well was seeded in 96-well cell assay plates. Two replicate plates for each combination.

Day 2, test compound addition:
Test compounds were tested at nine concentrations, either 5 µM to 0.00076 µM or 10 µM to 0.0015 µM, in a 1:3 dilution series. Sorafenib was tested at seven concentrations, 20 µM to 0.3 1 µM, in a 1:2 dilution series. The four dilution plates were prepared with the Echo instrument.

The compound dilutions were 2 times the desired final concentrations. The volume in the dilution plates in each well are 125 µl of medium with compounds.

100 µl from the dilution plate with compounds in the different concentrations were transferred to the corresponding well of the cell assay plate with 100 µl, (200 µl/well in total volume). Incubate the plates for 6 days, at 37° C., 5% $CO_2$.

Day 7, Reading of plates:
10 µl of CCK Kit-8 was added to each well using a multi-channel pipette (submerging the tips below the surface in each well). Plates were incubated for 4 hours at 37° C., 5% $CO_2$.

Sealing tape was put on top of the plate and the plate content was mixed gently.

The plate was read in the spectrophotometer at a wavelength of 450 nm, with a reference filter of 650 nm. Average absorbance was >1 to <3 for the vehicle treated cell controls.

Raw data from the two plates of each combination were entered into the Mac Synergy II shareware where the combined effect was calculated and plotted in a 3D dose-response surface graph. Theoretical additive interactions are calculated from the dose response curves for each drug individually. Calculated additive surface is subtracted from experimentally determined dose-response surfaces to reveal regions of non-additive activity. The final results are given as synergy or antagonism volumes ($\mu M^2\%$) according to guide lines given in the manual for MacSynergy II:

Synergy volumes:
1. Values of synergy or antagonism under 25 $\mu M^2\%$ (log volumes <2) at 95% confidence should be regarded as insignificant and are probably not important.
2. Values between 25 $\mu M^2\%$ and 50 $\mu M^2\%$ (log volumes >2 and <5) should be considered a minor but significant amount of synergy.
3. Values between 50 $\mu M^2\%$ and 100 $\mu M^2\%$ (log volumes >5 and <9) indicate moderate synergy or antagonism. This interaction may be important in vivo.
4. Values over 100 $\mu M^2\%$ (log volumes >9) indicate strong synergy and are probably important in vivo.

General Procedure for In Vivo Evaluation of Combinations of Sorafenib and a Troxacitabine Phosphoramidate Prodrug The effects of troxacitabine phosphoramidate prodrug treatment in combination with sorafenib can be assessed in vivo in subcutaneous xenograft models of hepatocellular carcinoma (HCC). The models are based on inoculating HCC cells (e.g. Hep3B, Huh-7 or HepG2) into the left flank of immunocompromised mice. Tumour volume is assessed app. three times per week and treatment with compound is typically initiated at a tumour size of 100-200 mm³. A typical study consist of 4 groups (n=10 mice/group);

1) vehicle (control), 2) troxacitabine phosphoramidate prodrug, 3) sorafenib alone and 4) troxacitabine phosphoramidate prodrug in combination with sorafenib.

Troxacitabine phosphoramidate prodrug is given via oral gavage at doses of 25-100 mg/kg once or twice daily for a period of 5-21 days. Alternatively for prodrugs with rapid metabolism in rodent blood, synergy can be modelled by administering troxacitabine parent intraperitoneally (i.p.) at doses of 2.5-25 mg/kg once or twice daily. Sorafenib is given via oral gavage once daily at doses of 10-50 mg/kg for a total period of 21 days. Tumour growth is assessed during the course of the treatment period and following cessation of treatment if applicable. Tumour growth inhibition and tumour growth delay is calculated and statistical analysis performed to assess significant effects of treatment compared to the control group.

Example 1

Figure 1B:
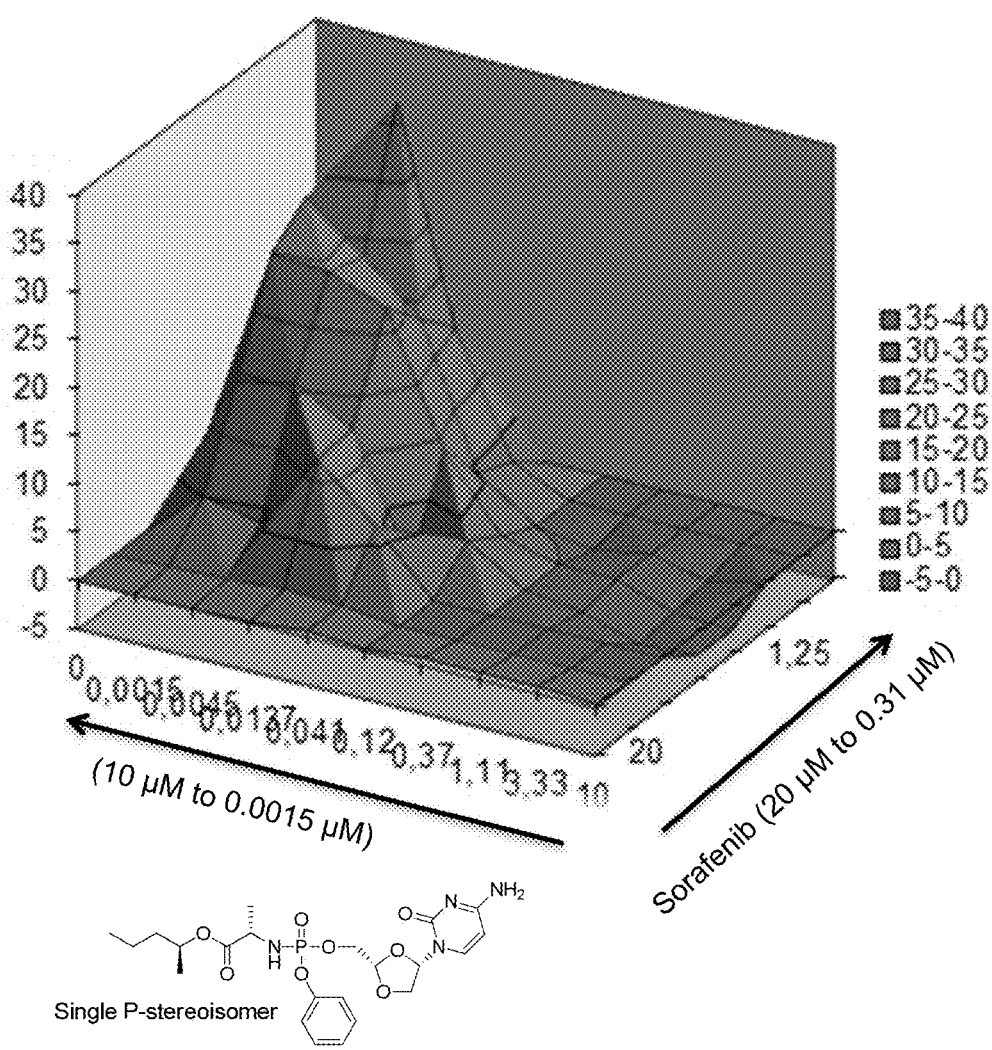

Sorafenib and the phosphoramidate prodrug of troxacitabine with the formula:

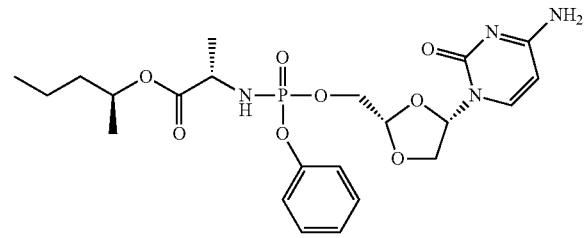 [SMILES: CCC[C@H](C)OC(=O)[C@H](C)NP(=O)(OC[C@H]1OC[C@@H](n2ccc(N)nc2=O)O1)Oc1ccccc1]

which is a single stereoisomer at the phosphorus atom, were assayed in the above combinatorial cell culture assay. FIG. 1A depicts the cytotoxic activities measured for each concentration permutation of the two compounds. FIG. 1B represents the 3D-synergy plot calculated by MacSynergy II, and concluding a log volume of 76 at 95% confidence, which corresponds to strong anti-proliferative synergy.

Example 2

Figure 2A:
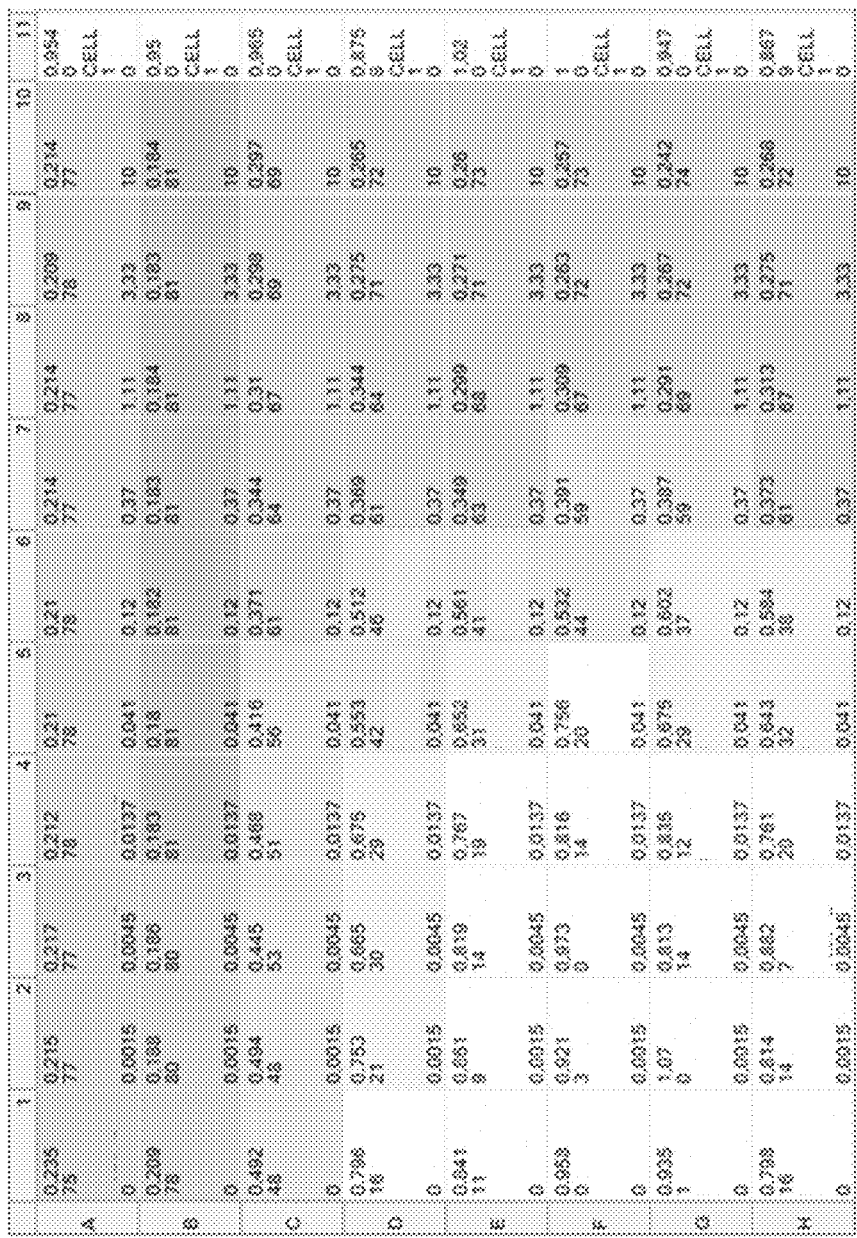
FIG. 2A represents a drug concentration/activity array of the combination of sorafenib and the single phosphorus stereoisomer of phosphoramidate prodrug of troxacitabine denoted (2S)—(R)-sec-butyl 2-(((((2S,4S)-4-(4-amino-5-fluoro-2-oxopyrimidin-1(2H)-yl)-1,3-dioxolan-2-yl) methoxy)-(phenoxy)phosphoryhamino)propanoate.
Figure 2A:
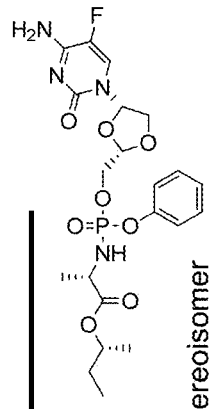
Figure 2B:
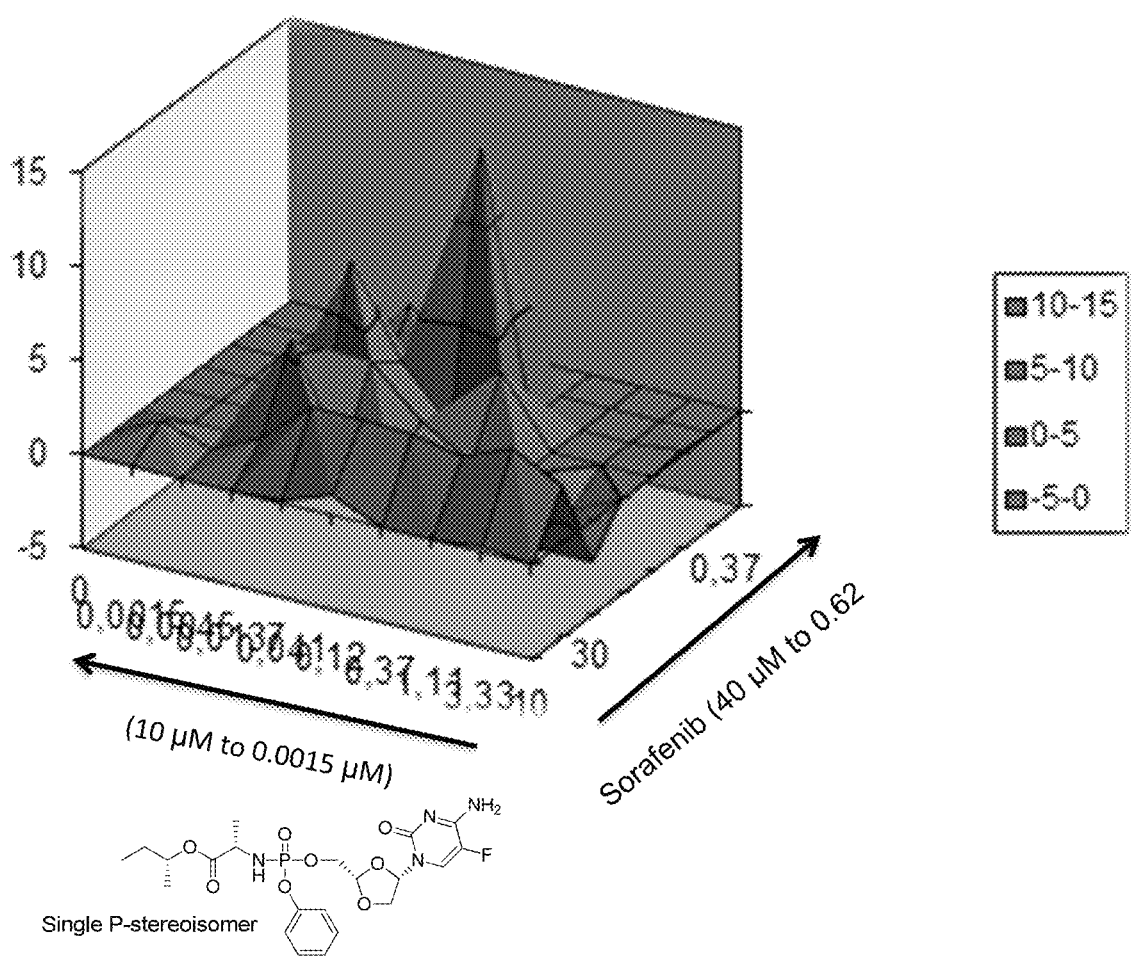
FIG. 2B represents the i3D-synergy plot derived from the data of FIG. 2A.

Sorafenib and the phosphoramidate prodrug of troxacitabine with the formula:

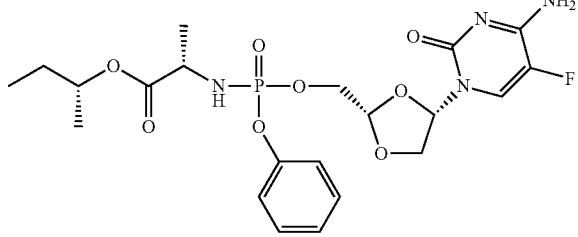

which is a single stereoisomer at the phosphorus atom, were assayed in the above combinatorial cell culture assay. FIG. 2A depicts the cytotoxic activities measured for each concentration permutation of the two compounds. FIG. 2B represents the isobologram calculated by MacSynergy II, and concluding a log volume of 11 at 95% confidence, which corresponds to strong anti-proliferative synergy.

Example 3

Figure 3A:
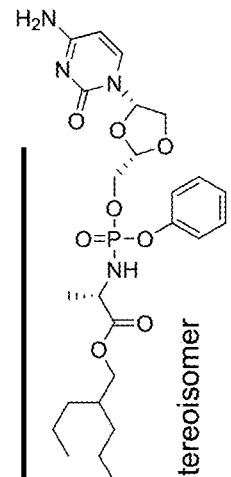
FIG. 3A represents a drug concentration/activity array of the combination of sorafenib and the single phosphorus stereoisomer of phosphoramidate prodrug of troxacitabine denoted (2S)-2-propylpentyl 2-(((((2S,4S)-4-(4-amino-2-oxopyrimidin-1(2H)-yl)-1,3-dioxolan-2-yl)methoxy)(phenoxy)phosphoryl)amino)propanoate.
Figure 3B:
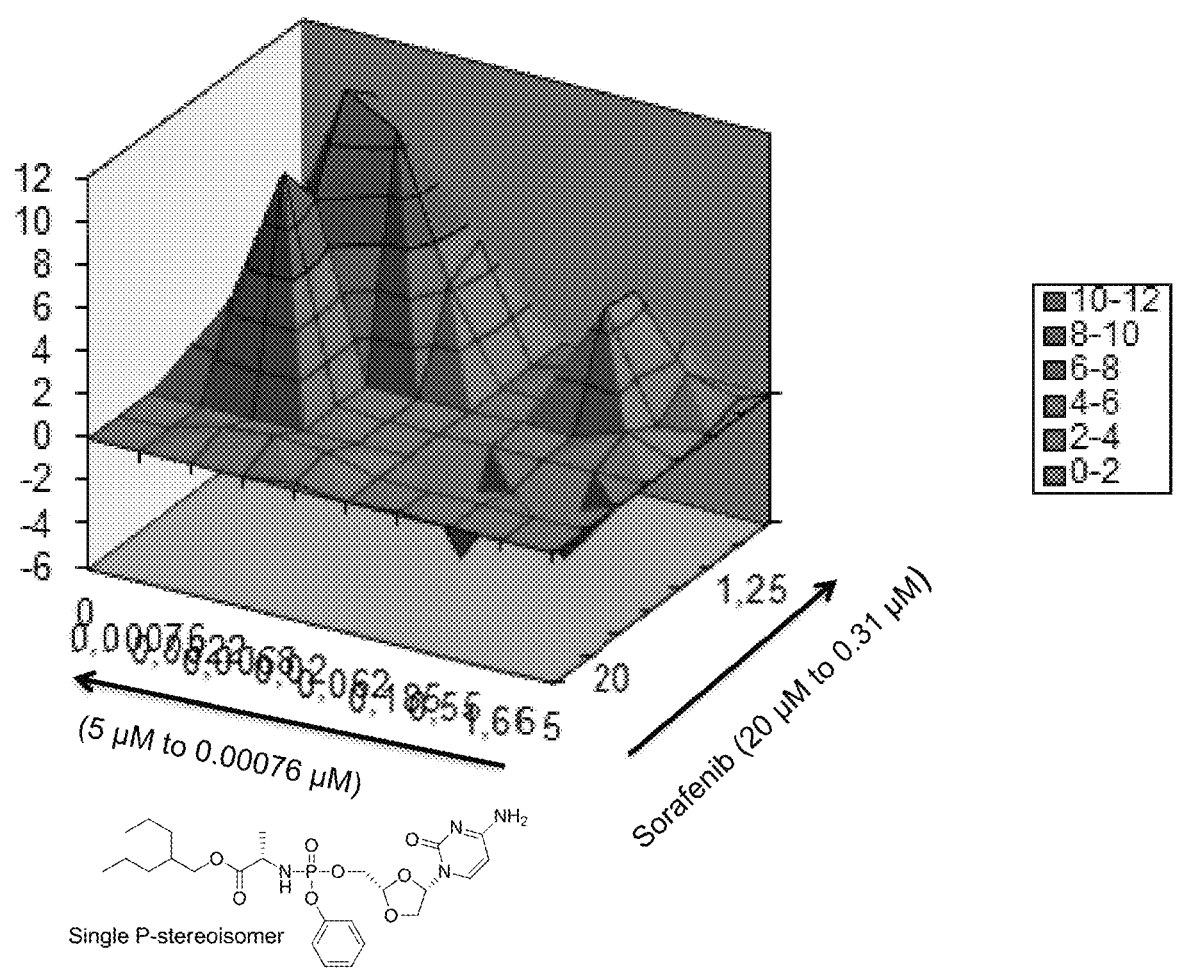
FIG. 3B represents the i3D-synergy plot derived from the data of FIG. 3A.

Sorafenib and the phosphoramidate prodrug of troxacitabine with the formula:

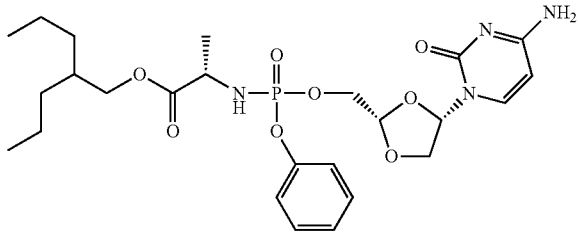 [SMILES: CCCC(CCC)COC(=O)[C@H](C)NP(=O)(OC[C@H]1OC[C@@H](n2ccc(N)nc2=O)O1)Oc1ccccc1]

which is a single stereoisomer at the phosphorus atom, were assayed in the above combinatorial cell culture assay. FIG. 3A depicts the cytotoxic activities measured for each concentration permutation of the two compounds. FIG. 3B represents the 3D-synergy plot calculated by MacSynergy II, and concluding a log volume of 32 at 95% confidence, which corresponds to strong anti-proliferative synergy.

Example 4

Figure 4A:
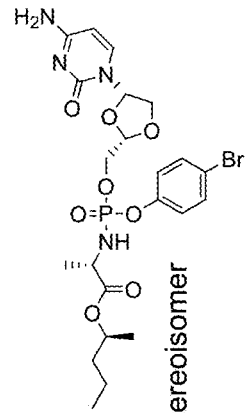
FIG. 4A represents a drug concentration/activity array of the combination of sorafenib and the single phosphorus stereoisomer of phosphoramidate prodrug of troxacitabine denoted (2S)—(S)-pentan-2-yl 2-(((((2S,4S)-4-(4-amino-2-oxopyrimidin-1(2H)-yl)-1,3-dioxolan-2-yl)methoxy)(4-bromophenoxy)phosphoryhamino)propanoate.
Figure 4B:
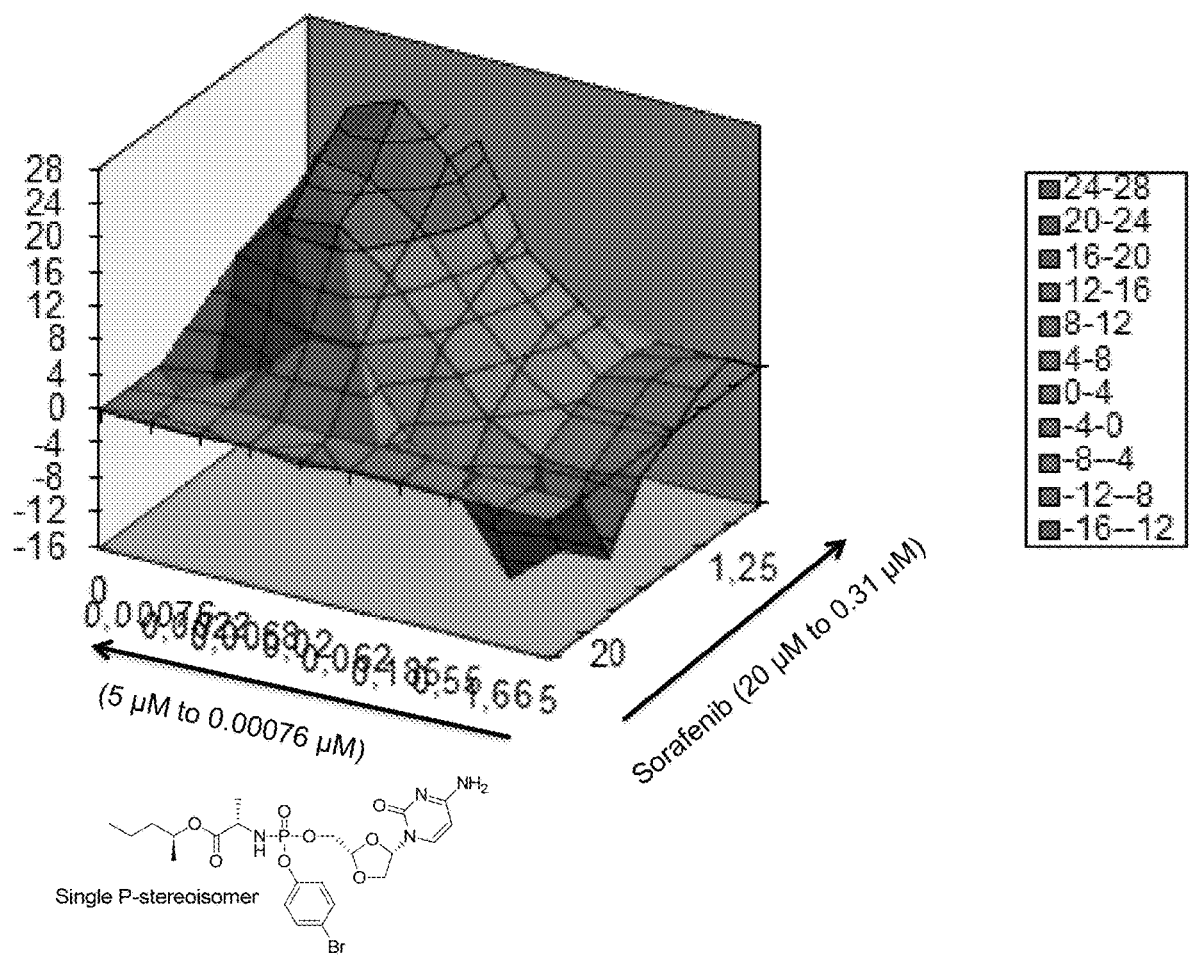
FIG. 4B represents the i3D-synergy plot derived from the data of FIG. 4A.

Sorafenib and the phosphoramidate prodrug of troxacitabine with the formula:

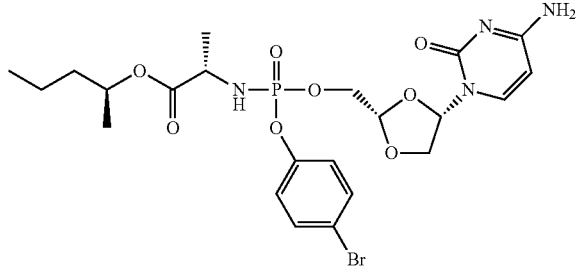 [SMILES: CCC[C@H](C)OC(=O)[C@H](C)NP(=O)(OC[C@H]1OC[C@@H](n2ccc(N)nc2=O)O1)Oc1ccc(Br)cc1]

which is a single stereoisomer at the phosphorus atom, were assayed in the above combinatorial cell culture assay. FIG. 4A depicts the cytotoxic activities measured for each concentration permutation of the two compounds. FIG. 4B represents the isobologram calculated by MacSynergy II, and concluding a log volume of 40 at 95% confidence, which corresponds to strong anti-proliferative synergy.

Example 5

Figure 5A:
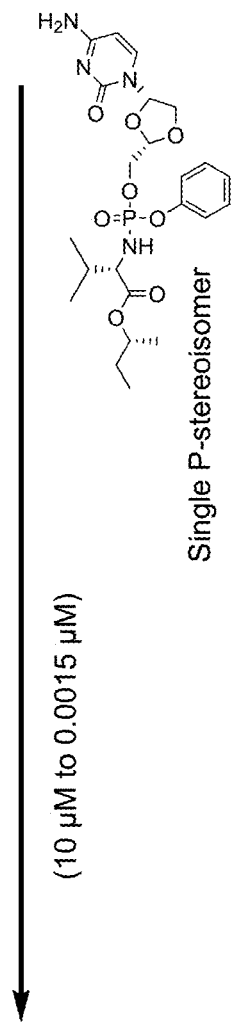
FIG. 5A represents a drug concentration/activity array of the combination of sorafenib and the single phosphorus stereoisomer of phosphoramidate prodrug of troxacitabine denoted (2S)—(R)-sec-butyl 2-(((((2S,4S)-4-(4-amino-2-oxopyrimidin-1(2H)-yl)-1,3-dioxolan-2-yl)methoxy)(phenoxy)phosphoryl)amino)-3-methylbutanoate.
Figure 5B:
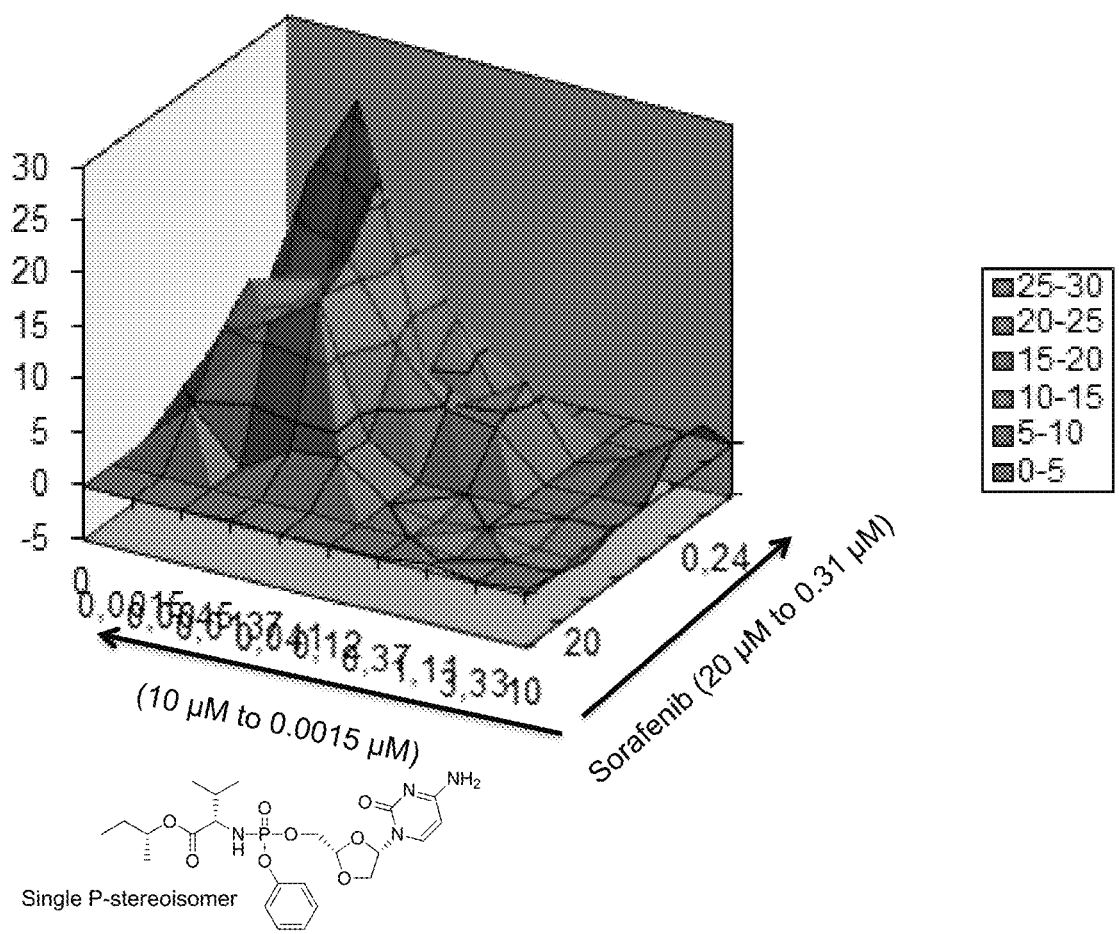
FIG. 5B represents the i3D-synergy plot derived from the data of FIG. 5A.

Sorafenib and the phosphoramidate prodrug of troxacitabine with the formula:

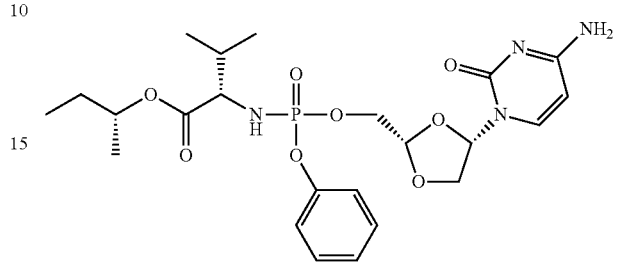

which is a single stereoisomer at the phosphorus atom, were assayed in the above combinatorial cell culture assay. FIG. 5A depicts the cytotoxic activities measured for each concentration permutation of the two compounds. FIG. 5B represents the isobologram calculated by MacSynergy II, and concluding a log volume of 46 at 95% confidence, which corresponds to strong anti-proliferative synergy.

The invention claimed is:

1. A method for treatment of liver cancer or liver metastasis, comprising administering to a subject in need thereof a targeted therapeutic agent, wherein the targeted therapeutic agent is an isotope of sorafenib with the structural formula:

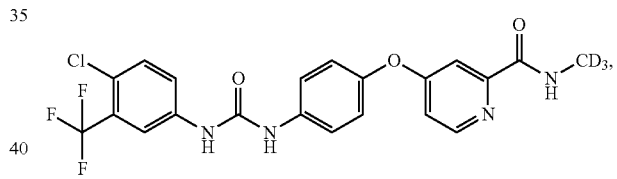

in combination with a phosphoramidate prodrug of troxacitabine with the formula:

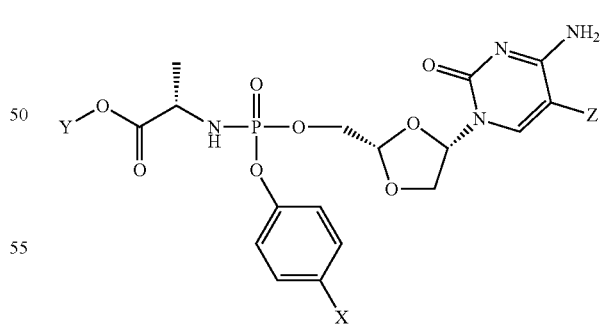

wherein
Y is $C_1$-$C_8$ straight or branched chain alkyl;
X is H, halo, $C_3$-$C_4$cycloalkyl or $C_1$-$C_4$alkyl; and
Z is H or fluoro,
or a pharmaceutically acceptable salt thereof.

2. The method according to claim 1, wherein the phosphoramidate prodrug of troxacitabine has the stereochemistry:

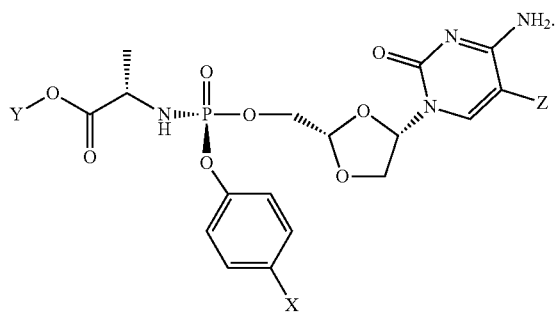

3. The method according to claim 1, wherein Z is H.

4. The method according to claim 1, wherein:
a) X is H, Y is 2-propylpentyl, and Z is H;
b) X is H, Y is (S)-pentan-2-yl, and Z is H;
c) X is Br, Y is (S)-pentan-2-yl, and Z is H;
d) X is H, Y is (R)-sec-butyl, and Z is H;
e) X is H, Y is 2-ethylbutyl, and Z is H;
f) X is cyclopropyl, Y is (S)-pentan-2-yl, and Z is H; or
g) X is t-butyl, Y is (S)-pentan-2-yl, and Z is H.

5. The method according to claim 1, wherein the sorafenib isotope and the phosphoramidate prodrug of troxacitabine are each administered daily on the same day.

6. The method according to claim 5, wherein the sorafenib isotope and the phosphoramidate prodrug of troxacitabine are co-delivered in a common, orally administered dosage unit.

7. The method according to claim 5, wherein sorafenib isotope and the phosphoramidate prodrug of troxacitabine are administered as separate orally administered dosage units.

8. The method according to claim 7, wherein the dosage unit(s) of sorafenib isotope and the dosage unit(s) of the phosphoramidate prodrug of troxacitabine are administered at least 6 hours apart on any given day.

9. The method according to claim 1, wherein the sorafenib isotope and the phosphoramidate prodrug of troxacitabine are alternately administered in monotherapy treatment cycles of 1-28 days.

10. The method according to claim 9, wherein treatment commences with a sorafenib isotope cycle.

11. The method according to claim 1, wherein the liver cancer is HCC or intra-hepatic cholangiocarcinoma.

12. The method according to claim 1, wherein the liver metastasis is derived from colorectal cancer.

13. The method according to claim 1, wherein the liver metastasis is derived from breast cancer, esophageal cancer, lung cancer, melanoma, pancreatic cancer or stomach cancer.

14. The method according to claim 5, wherein the sorafenib isotope and the phsophoramidate prodrug of troxacitabine are each administered daily as QD, BID or TID on the same day.

15. The method according to claim 9, wherein the sorafenib isotope and the phsophoramidate prodrug of troxacitabine are alternately administered in monotherapy treatment cycles of 1-28 days, and are interspersed with treatment-free periods of 1-28 days.

* * * * *